(12) United States Patent
Borer et al.

(10) Patent No.: US 8,080,379 B2
(45) Date of Patent: Dec. 20, 2011

(54) BRANCHED AND MULTI-CHAIN NUCLEIC ACID SWITCHES FOR SENSING AND SCREENING

(75) Inventors: Philip N. Borer, Chittenango, NY (US); Bruce S. Hudson, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 12/901,762

(22) Filed: Oct. 11, 2010

(65) Prior Publication Data

US 2011/0059555 A1   Mar. 10, 2011

Related U.S. Application Data

(60) Division of application No. 12/401,498, filed on Mar. 10, 2009, now Pat. No. 7,829,287, which is a continuation of application No. 11/195,547, filed on Aug. 2, 2005, now Pat. No. 7,521,546.

(60) Provisional application No. 60/598,498, filed on Aug. 3, 2004.

(51) Int. Cl.
  *C12Q 1/68* (2006.01)
(52) U.S. Cl. ........................ 435/6.1; 435/6.19
(58) Field of Classification Search ................ 435/6, 7.1
  See application file for complete search history.

(56) References Cited

U.S. PATENT DOCUMENTS

| | | | |
|---|---|---|---|
| 5,496,938 A | 3/1996 | Gold et al. | |
| 5,786,462 A | 7/1998 | Schneider et al. | |
| 5,821,046 A | 10/1998 | Karn et al. | |
| 5,925,517 A | 7/1999 | Tyagi et al. | |
| 6,451,588 B1 | 9/2002 | Egholm et al. | |
| 6,555,326 B1 * | 4/2003 | Lustig et al. | 435/7.8 |
| 6,569,630 B1 | 5/2003 | Vivekananda et al. | |
| 6,680,377 B1 | 1/2004 | Stanton et al. | |
| 2003/0087239 A1 | 5/2003 | Stanton et al. | |

(Continued)

FOREIGN PATENT DOCUMENTS

WO  WO 99/31276  6/1999

(Continued)

OTHER PUBLICATIONS

DeBaar, et al. "Detection of Human Immunodeficiency Virus Type 1 Nucleocapsid Protein p7 In Vitro and In Vivo," *Journal of Clinical Microbiology*, vol. 37, No. 1, pp. 63-67, Jan. 1999.

(Continued)

*Primary Examiner* — Kenneth R. Horlick
(74) *Attorney, Agent, or Firm* — Knobbe, Martens, Olson & Bear, LLP

(57) ABSTRACT

Embodiments of the invention relate to a branched or multi-chain nucleic acid switch adapted to switch from a first conformation to a second conformation upon ligand binding. The switch includes a probe strand, P, which includes the ligand binding domain; a switching framework which includes a cover strand (C), and a tether that holds P and C together and a signaling apparatus. Some embodiments include a toggle strand (T) where now the tether holds P, C, T, and the signaling apparatus together. As the switch changes between the first and second conformations; the signaling apparatus reports the state of the switch. The signaling entity is typically a lumiphore and a quencher located along the switching framework. Nucleic acid switches have applications in real time assays for diverse agents including infectious agents, environmental toxins, and terrorist agents, as well as screening methods for such agents. Further applications are found for nanoelectronics, nanofabrication and nanomachines.

20 Claims, 16 Drawing Sheets

U.S. PATENT DOCUMENTS

2003/0165837 A1    9/2003    Boger
2005/0064471 A1    3/2005    Griffey et al.

FOREIGN PATENT DOCUMENTS

WO    WO 03/054223    7/2003
WO    WO 2004/069850    8/2004

OTHER PUBLICATIONS

Kim, et al. "Selection and Stabilization of the RNA Aptamers Against the Human Immunodeficiency Virus Type-1 Nucleocapsid Protein," *Biochemical and Biophysical Research Communication*, vol. 291, pp. 925-931, 2002.

Nutiu, et al. "Structure-Switching Signaling Aptamers: Transducing Molecular Recognition into Fluorescence Signaling," *Chem. Eur. J.*, vol. 10, pp. 1868-1876, 2004.

Yamamoto, et al. "Molecular Beacon Aptamer Fluoresces in the Presence of TAT Protein HIV-1," *Genes to Cells*, vol. 5, pp. 389-396, 2000.

Fraudendorf, et al. "Detection of Small Organic Analytes by Fluorescing Molecular Switches," *Bioorganic & Med. Chem*, vol. 9, pp. 2521-2524, 2001.

Jose, et al. "Cooperative Binding of Effectors by an Allosteric Ribozyme," *Nucleic Acid Research*, vol. 29, No. 7, pp. 1631-1637, 2001.

Soukup, et al. "Nucleic Acid Molecular Switches," *Trends in Biotechnology*, vol. 17, No. 12, pp. 469-476, 1999.

Sekella, et al. "A Biosensor for Theophylline Based on Fluorescence Detection of Ligand-Induced Hammerhead Ribozyme Cleavage," *RNA*, vol. 8, pp. 1242-1252, 2002.

Shubsda, et al. "Affinities of Packaging Domain Loops in HIV-1 RNA for the Nucleocapsid Protein," *Biochemistry*, vol. 41, pp. 5276-5282, 2002.

Ben-Asouli, et al. "Recognition of 5'-Terminal TAR Structure in Human Immunodeficiency Virus-1 mRNA by Eukaryotic Translation Initiation Factor 2," *Nucleic Acids Research*, vol. 28, No. 4, pp. 1011-1018, 2000.

Tyagi, et al. "Molecular Beacons: Probes that Fluoresce upon Hybridization," *Nature Biotechnology*, vol. 14, pp. 303-308, Mar. 1, 1996.

Hartig, et al. "Reporter Ribozymes for Real-time Analysis of Domain-specific Interactions in Biomolecules: HIV-1 Reverse Transcriptase and the Primer Template Complex," *Angew. Chem. Int. Ed.*, vol. 41, No. 22, 9pp. 4263-4266, 2002.

Jayasena, "Aptamers: An Emerging Class of Molecules that Rival Antibodies in Diagnostics," *Clinical Chemistry*, vol. 45, No. 9, pp. 1628-1650, Jan. 1, 1999.

Supplementary European Search Report dated Apr. 22, 2009.

\* cited by examiner

```
           A  Combimer  B
    P   s'_11...11|33...33|22...22
    C      222...22|44...44|11...11_s
    T   s"_111...11|4x...44|22...22
```

BRANCHED AND MULTI-CHAIN NUCLEIC ACID SWITCHES FOR SENSING AND SCREENING

CROSS-REFERENCE TO RELATED APPLICATIONS

This application is a divisional of U.S. application Ser. No. 12/401,498, filed, Mar. 10, 2009, now U.S. Pat. No. 7,829,287, issued Nov. 9, 2010; which is a continuation of U.S. application Ser. No. 11/195,547, filed Aug. 2, 2005, now U.S. Pat. No. 7,521,546, issued Apr. 21, 2009, which claims priority to U.S. Provisional application No. 60/598,498, filed Aug. 3, 2004. All of the above applications are incorporated herein by reference.

STATEMENT REGARDING FEDERALLY SPONSORED R&D

This work was supported in part by NIH grant R42GM68413 to OrthoSystems, Inc. which has a subcontract to Syracuse University. Consequently, the U.S. government may have certain rights to this invention.

REFERENCE TO SEQUENCE LISTING, TABLE, OR COMPUTER PROGRAM LISTING

A sequence listing is annexed hereto.

BACKGROUND OF THE INVENTION

1. Field of the Invention

The disclosed embodiments relate to nucleic acid constructs and methods of using these constructs to rapidly detect target molecule interactions. The switches can have applications in sensing the presence of targets, including proteins, nucleic acids, organisms, environmental contaminants, bioterror agents, and/or pharmaceutical agents. The switches should facilitate processes to screen lead compounds for drug development that have high affinity for a target molecule and/or target complex. Embodiments of the invention to screen potential drugs effective against HIV-1 are used to illustrate the invention. The molecular switches are also applicable to processes in molecular electronics and nanodevices.

2. Description of the Related Art

HIV-disease causes great suffering and death in the U.S., and millions are dying worldwide. Even though the number of deaths in the United States from HIV-disease has declined in recent years, the worldwide epidemic is out of control. This ever-larger number of infected people is a direct threat to everyone because HIV-1 mutates so rapidly. The larger the pool of infected individuals, the more rapidly drug-resistant strains will emerge. The reverse transcriptase makes so many errors that every single point mutation occurs daily in newly infected cells (Coffin, J. M. (1995) *Science* 267:483-9), and nearly 1% of all possible double mutations occur (Perelson, A. S. et al. (1997) *AIDS* 11 (suppl. A) S17-34). Combinations of drugs used in "Highly Active AntiRetroviral Therapy" (HAART) treatment regimes target different parts of the viral life cycle. In the face of such a high mutation rate, it is clear that failures in the HAART approach must occur with increasing frequency using existing drugs. Resistant strains already exist for all currently used protease and reverse transcriptase inhibitors (Pillay, D. et al. (2000) *Rev. Med. Viral.* 10:231-53), the most potent weapons in the battle against AIDS.

Even if an effective vaccine is developed to prevent new HIV-1 infections, there will still remain a need to treat millions of AIDS victims. Their long-term treatment will require new generations of drugs. Anti-nucleocapsid protein drugs, as well as agents directed at other potential HIV targets, such as anti-rev and anti-tat, could be combined with current and next generation drugs for a multi-pronged attack that would be difficult for the virus to evade. Adding these drugs to present HAART treatments may provide highly specific and potent antiretroviral treatments. Such drugs may greatly diminish the devastating effects of HIV-related disease around the world.

Scores of other human and animal disease states have been related to interactions of biomolecules with other molecules. These biomolecules present targets for therapeutic intervention. This is a current focus for many academic and industrial efforts to generate new pharmaceuticals. The current invention can accelerate drug discovery. Examples include, but are not limited to, kinases and phosphatases involved in signaling cascades.

Detection of environmental contaminants and terrorist agents has become an important focus of public concern. The current invention can be applied to the detection of most agents that interest the Environmental Protection Agency (EPA) (http://www.epa.gov/safewater/mcl.html#mcls) and on the select agents list monitored by the Centers for Disease Control (CDC), the National Institute of Allergy and Infectious Diseases (NIAID) (http://www2.niaid.nih.gov/Biodefense/bandc_priority.htm), and the Homeland Security Agency (HSA). The current invention provides a technology for near real-time detection of environmental and terrorist agents. Examples include, but are not limited to, *cryptosporidium* and *giardia*, which contaminate public water supplies, and ricin, anthrax and ebola virus, which are agents for bioterrorism and bio-warfare.

Molecules that can switch between stable states are of interest for nanoelectronics, nanofabrication, and nanomachines. The present invention is of special interest in high density information storage devices used in nanoelectronic applications. Read, write, and erase functions can be constructed using the subject invention. It is also contemplated that subject molecular switches could be coupled to build materials and machines on the molecular scale.

SUMMARY OF THE INVENTION

Embodiments of the invention are directed to a branched or multichain nucleic acid switch adapted to switch from a first conformation to a second conformation upon ligand binding. The switch may include one or more of the following elements:

a probe strand P which includes at least one ligand binding domain;

a switching framework which includes a cover strand (C);

a tether that holds P and C together while the switch changes between the first and second conformations; and a signaling apparatus which includes a combination of signaling entities.

Preferably, the probe strand is DNA, RNA, modified nucleic acid, or combinations thereof. In preferred embodiments, the first conformation has P extensively hybridized to C and the second conformation has P not hybridized to C. Preferably, C is at least 50% complementary to P. More preferably, C is completely complementary to P.

In preferred embodiments, the signaling entities include a lumiphore and a quencher located along the switching framework.

In preferred embodiments, the branched or multichain switch also includes a toggle strand (T). Preferably, T is at least 50% complementary to P.

In preferred embodiments, the branched or multichain switch also includes a fastener, F, to couple two nucleic acid strands together. Preferably, the first strand includes C and the second strand includes P when the branched or multichain switch is in the second conformation.

In preferred embodiments, the ligand binding domain of the branched or multichain switch includes a naturally occurring RNA binding site or analog thereof or a naturally occurring DNA binding site or analog thereof or a combinatorially derived sequence or related fragment.

Preferably, the ligand binding domain of the branched or multichain switch is adapted to bind a ligand which is selected from:

a disease agent, such as an agent from a disease including but not limited to Hepatitis C, Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, HIV-1, MMTV, HIV-2, HTLV-1, SNV, BIV, BLV, EIAV, FIV, MMPV, Mo-MLV, Mo-MSV, M-PMV, RSV, SIV, or AMV;

a retroviral component including but not limited to TAR-tat, RRE-rev, DIS, PBS, RT, PR, IN, SU, TM, vpu, vif, vpr, nef, mos, tax, rex, sag, v-src, v-myc and precursors and protease products of the precursors, gag, gag-pol, env, src, or one;

a toxin or other factor derived from bacteria or other microorganisms including but not limited to *B. anthracis, Burkholderia pseudomallei, Botulinum, Brucellosis, Candida albicans, Cholera, Clostridium perfringins, Kinetoplasts, Malaria, Mycobacteria, Plague, Pneumocystis, Schistosomal parasites, Cryptosporidium, Giardia, Ricin, Saxitoxin, Shiga Toxin, Staphylococcus* (including enterotoxin B), Trichothecene mycotoxins, Tularemia, or agents causing Toxoplasmosis; and nerve gas agents, chemical poisons, contaminants of water supplies, contaminants of food and beverages, or contaminants of air.

Embodiments of the invention are directed to populations of branched or multichain switch molecules which include P and C and optionally T. Preferably, there are more molecules with C hybridized to P than with P not hybridized to C. In other preferred embodiments, there are more molecules with C hybridized to P than with T hybridized to C.

In preferred embodiments of the branched or multichain switch, P, C and T are joined together at a vertex.

Embodiments of the invention are directed to methods to generate the branched or multichain switches described above by adjusting the equilibrium constant, K1, for the switch from the first conformation to the second conformation. In preferred embodiments, the sequence of C is altered, and the free energy difference between the two conformations, is used to estimate K1. In preferred embodiments, K1 is set to favor conformation 1. Preferably, the value of K1 can be experimentally verified. In preferred embodiments, a signal of a candidate switch is used to determine the candidate's value of K1 by interpolation between that for sequence (a), which favors conformation 1 over conformation 2 by a factor of 100 or more, and sequence (b), which favors conformation 2 over conformation 1 by a factor of 100 or more. In preferred embodiments, the value of K1 for switch candidates is estimated by comparison with known competitors, X, of the ligand, L, designed to interact with conformation 2 of the switch.

Embodiments of the invention are directed to methods to generate the branched or multichain switches which include P, C, and T which include at least one of the following steps:

adjusting an equilibrium constant, K1, for the switch from the first conformation to the second conformation;

altering sequences of C and T; and estimating K1, based upon the free energy difference between the two conformations.

Embodiments of the invention are directed to a kit which includes the branched or multichain switch including P, C, and optionally, T for real time detection of a selected ligand.

Embodiments of the invention are directed to methods of chemical screening which include one or more of the following steps:

providing a bistable branched or multichain switch, which includes an analog of an RNA or DNA, wherein the analog includes the ligand binding domain, a molecular framework and a signaling apparatus;

contacting the branched or multichain switch with the ligand in the absence of a screened chemical entity;

monitoring a signal produced from the signaling apparatus in the absence of the chemical entity;

contacting the branched or multichain switch with the ligand in the presence of the chemical entity;

monitoring a signal produced from the signaling apparatus in the presence of the chemical entity; and comparing the signal produced in the absence of the chemical entity with the signal produced in the presence of the chemical entity to determine the effect of the chemical entity on the ligand binding.

In preferred embodiments, the signaling apparatus includes a lumiphore and a quencher of the lumiphore. In preferred embodiments, the ligand binding domain includes RNA, the molecular framework includes DNA and the ligand is a viral protein.

In preferred embodiments, the ligand binding domain includes RNA, the molecular framework includes DNA and the ligand binding domain includes a naturally occurring RNA binding site or analog thereof or a naturally occurring DNA binding site or analog thereof or a combinatorially derived sequence or related fragment. Preferred embodiments also include the step of equilibrating the molecular switch and the ligand prior to adding the chemical entity.

In preferred embodiments, the ligand binding domain includes RNA, the molecular framework includes DNA and the ligand is selected from:

a disease agent wherein the disease is Hepatitis C, Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, HIV-1, MMTV, HIV-2, HTLV-1, SNV, BIV, BLV, EIAV, FIV, MMPV, Mo-MLV, Mo-MSV, M-PMV, RSV, SIV, or AMV;

a retroviral component which is TAR-tat, RRE-rev, DIS, PBS, RT, PR, IN, SU, TM, vpu, vif, vpr, nef, mos, tax, rex, sag, v-src, v-myc and precursors and protease products of the precursors, gag, gag-pol, env, src, or one;

a toxin or other factor derived from bacteria or other microorganisms which are *B. anthracis, Burkholderia pseudomallei, Botulinum, Brucellosis, Candida albicans, Cholera, Clostridium perfringins, Kinetoplasts, Malaria, Mycobacteria, Plague, Pneumocystis, Schistosomal parasites, Cryptosporidium, Giardia, Ricin, Sax-* itoxin, Shiga Toxin, Staphylococcus (including enterotoxin B), Trichothecene mycotoxins, Tularemia, or agents causing Toxoplasmosis; and nerve gas agents, chemical poisons, contaminants of water supplies, contaminants of food and beverages, or contaminants of air.

Embodiments of the invention are directed to a molecular switch adapted to switch from a first energy state to a second energy state upon application of triggering photons, said switch including one or more of the following:

a photosensitive ligand binding domain which includes a combinatorially-derived sequence;

a molecular framework which includes the photosensitive ligand binding domain adapted to switch from a first stable conformation to a second stable conformation upon binding of the photosensitive ligand by the ligand binding domain; and a signaling apparatus along the molecular framework which includes a combination of signaling entities that vary upon application of the triggering photons when the molecular framework switches between first and second stable conformations.

Embodiments of the invention are directed to methods of using any of the molecular switches described above, including at least the steps of:

binding a ligand to the ligand binding domain in P, whereby the branched or multichain switch changes from the first conformation to the second conformation upon ligand binding; and measuring a luminescence change as a result of the conformational change.

Embodiments of the invention are directed to a branched or multichain switch adapted to switch from a first conformation to a second conformation upon ligand binding, said switch including a first strand which has a ligand binding domain; a second strand; and a fastener to couple the two strands together; wherein the first strand and second strand hybridize to each other in the first conformation and the ligand binding domain is free in the second conformation.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 2 shows the HIV-1 NCp7 protein (SEQ ID NO: 8). Residues carrying a charge at neutral pH are shown in outlined letters (positive=capitals, negative=lower-case); $Zn_2$.NCp7(1-55) carries a +9 charge at neutral pH.

(a) A 3-fold junction connects the P, C, T segments, and the designation T_C_P denotes the unpaired random-coil reference state for free energy comparisons.

(b) The bistable molecule can exist in either the T_C:P state or the T:C_P state. The ligand binding site in P is hidden (sequestered in a base-paired region) in T_C:P and open in T:C_P. The distances between the signaling entities, S, S', and S", change when the switch changes state.

(c) A free energy diagram depicts interconversion of states. The two forms of the switch convert rapidly if the intermediate steps occur via branch migration.

(d) The sequences of the three segments can be engineered to create an efficient molecular switch. A "1" denotes a nucleotide complementary to a "2", and "3" is complementary to "4". The "combimer" contains the ligand binding site, in P, which is written 5'-3', left to right. The cover segment, C, written 3'-5', can be slightly longer than P, but otherwise is depicted as fully complementary. The toggle segment, T, is depicted as having a mismatch with C in the combimer zone, but is otherwise fully complementary.

Figure 13A:
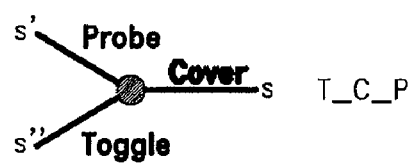
FIG. 13 illustrates the embodiment in which probe (P), cover (C), and toggle (T) strands are tethered at a single vertex, thus comprising a unimolecular switch.
Figure 13B:
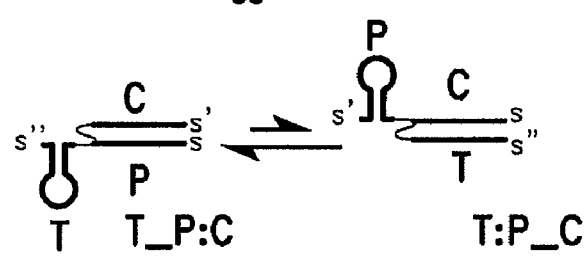
Figure 13C:
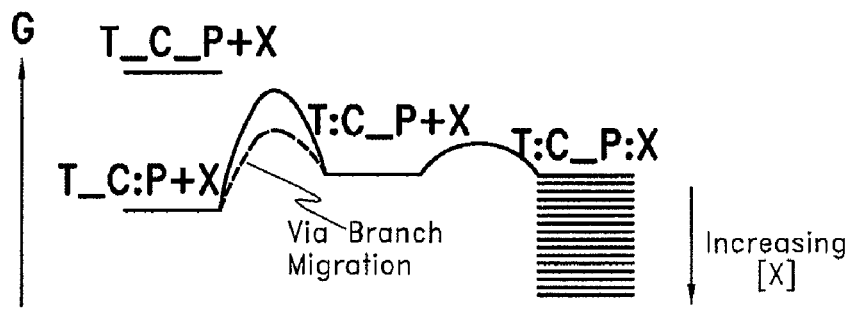
Figure 14A:
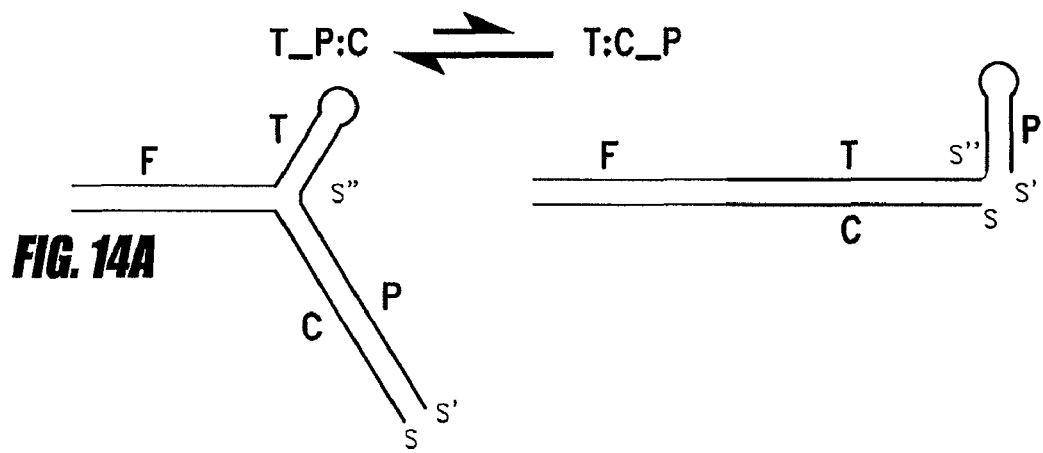
Figure 14B:
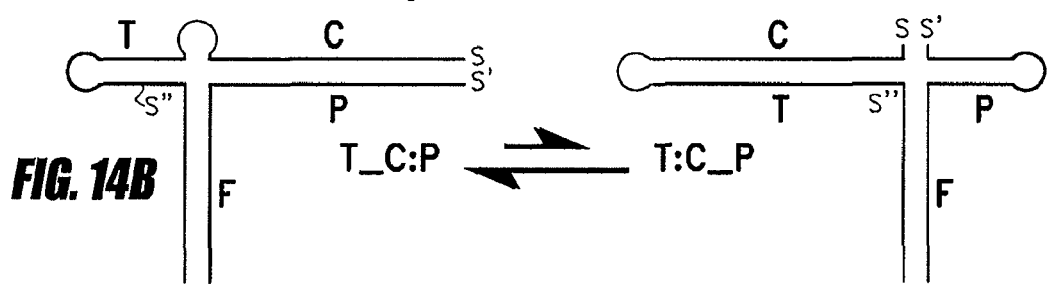

FIG. 14 illustrates three embodiments which are analogous to FIG. 13b. The fastener stem, F, is stable and does not substantially alter during switching events. P, C, and T have the same meaning as in FIG. 13. Locations of signaling moieties, S, S', and S" can be optimized to create the most robust signal output.

Figure 15:
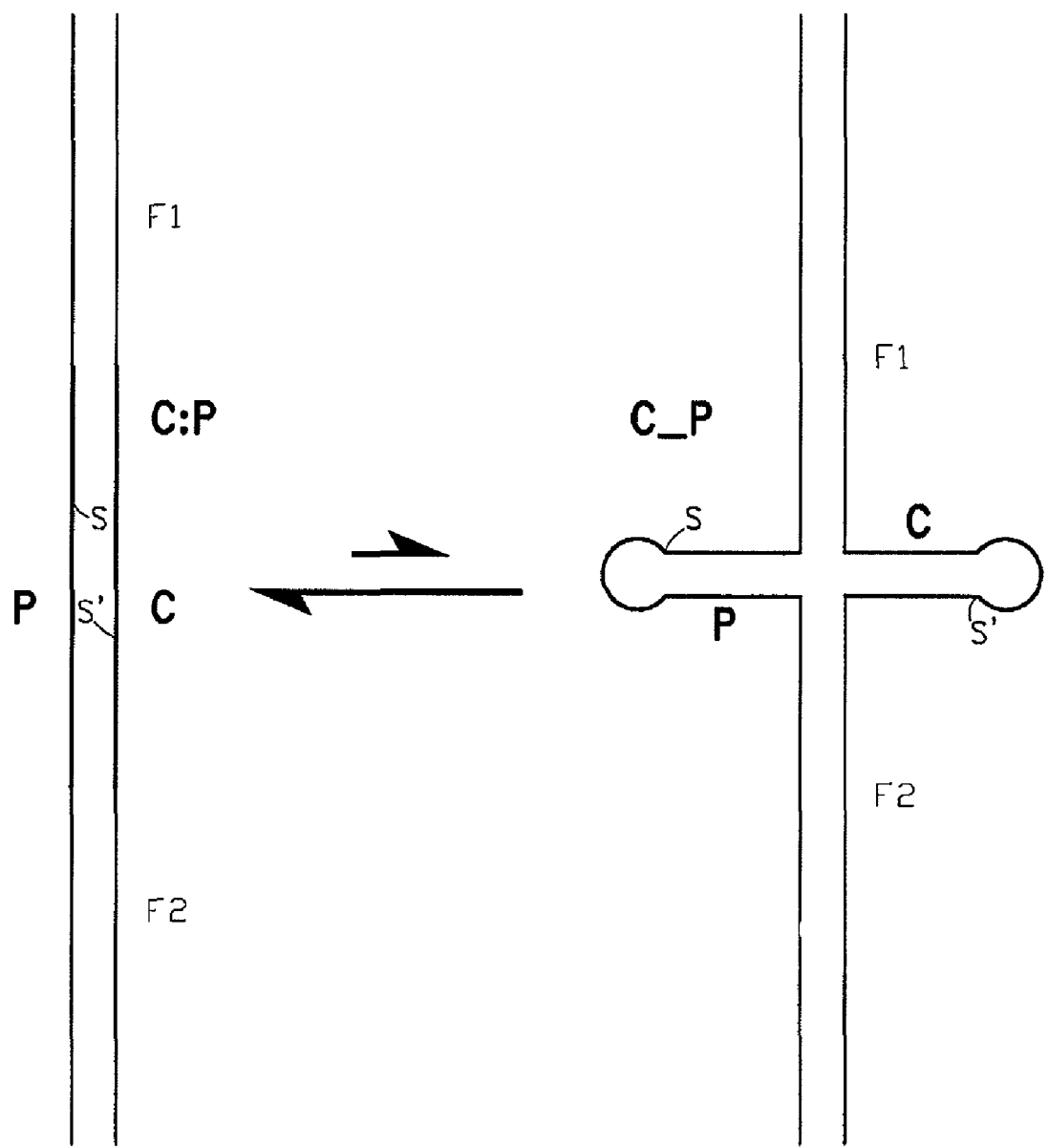

FIG. 15 illustrates an embodiment in which P and C lie on separate strands, which are held together by stable fastener stems, F1 and F2.

Figure 16:
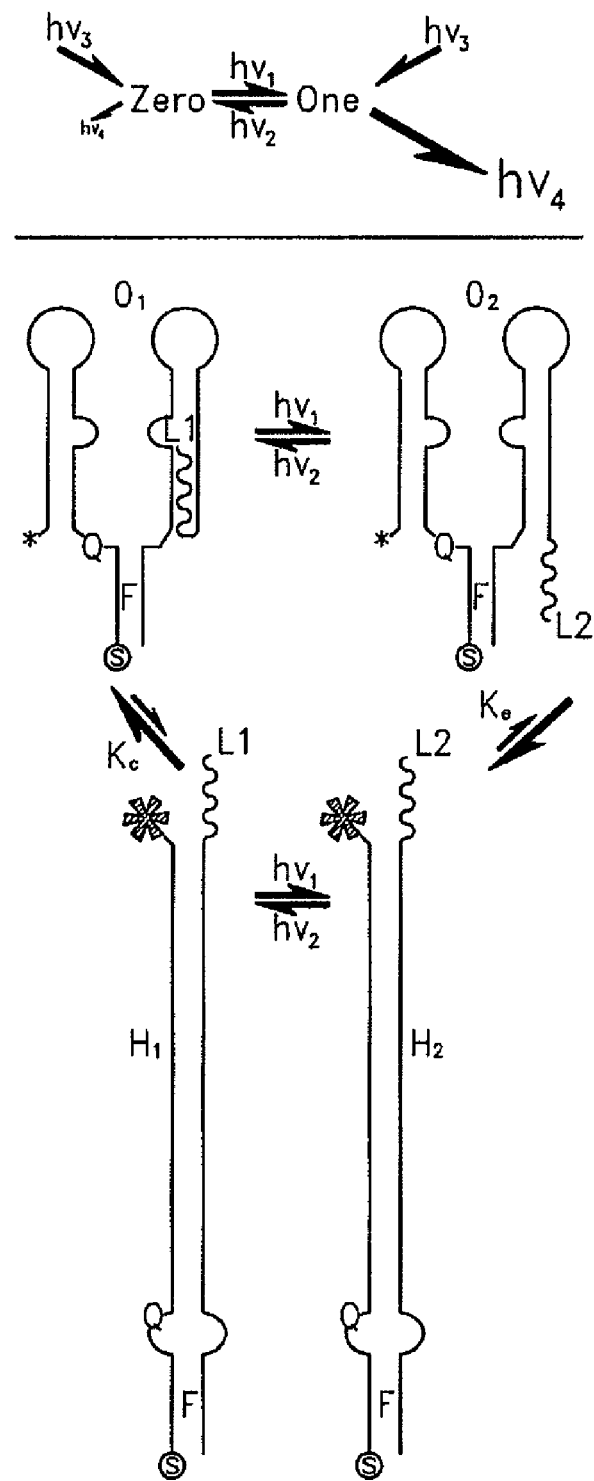

FIG. 16 shows a basic module for molecular electronic applications. Top: A preferred digital system has states "Zero" and "One", which are switched by application of light at frequencies $v_1$ (Write) and $v_2$ (Erase); the state of the system is interrogated at $v_3$ (Read) and detected at $v_4$. Bottom: Schematic of switchable nucleic acid constructs to support the preferred embodiment. S denotes a site for possible attachment to a solid support.

DETAILED DESCRIPTION OF THE PREFERRED EMBODIMENT

FRET stands for fluorescence resonance energy transfer,

The term, luminescence, is a broad term and is used to encompass all forms of the emission of light subsequent to excitation by light. This includes fluorescence as it is commonly encountered in FRET and molecular beacon technology where emission or quenching occurs within microseconds of excitation. It also encompasses longer-lived phosphorescence, and emission from lanthanides where spin-orbit coupling is so large that fluorescence and phosphorescence cannot be distinguished. Reference will often be made to molecular beacon technology using conventional fluorophores and quenchers. However, it is understood that the signaling apparatus is not limited to conventional fluorophores and quenchers; substitution of another excitation-emission scheme, such as with sensitized lanthanides and appropriate quenching moieties is also included within the scope of this invention.

A lumiphore is a chemical entity that produces luminescence, particularly a chemical entity that that absorbs electromagnetic energy, then emits energy by fluorescence, phosphorescence, or luminescence.

A refers to a bistable RNA and/or DNA construct (except where A is used to designate adenine in a nucleotide sequence), X refers to any molecule that competes with or otherwise interferes with binding of L to natural RNA or DNA analogs of A, L, L1, L2, etc. refer to a ligand molecules such as a protein, cell-surface feature, small molecule, or other chemical entity that binds to the O-form of a molecular switch, O refers to the open conformation of a switch molecule where the binding site is available to interact with the ligand, H refers to the switch conformation where the binding site is hidden, $K_1 = [O]/[H]$ refers to the $H \leftrightarrows O$ equilibrium constant, where [x] denotes the concentration of species, x, $K_2 = [L][O]/[L \cdot O]$ refers to the $L \cdot O \leftrightarrows L+O$ dissociation equilibrium constant, $K_3 = [L][X]/[L \cdot X]$ refers to the $L \cdot X \leftrightarrows L+X$ dissociation equilibrium constant, Q refers to a quencher in a conventional FRET or molecular beacon experiment, or where longer-lived luminescence is quenched,

*, D, D1, D2, etc. refer to a fluorescence donor in a FRET or molecular beacon experiment, or longer-lived excited states in luminescent donors, S, S', S", etc. refer to signaling moieties that include FRET donors and acceptors, luminescent constructs, etc., F, F1, F2, etc. refer to fastener duplex sequence(s) required for tethering separate strands of a molecular switch. These fixed sequences are not varied to optimize the performance of a switch, P refers to a probe segment that contains a ligand binding site in the O conformation of a molecular switch, C refers to a cover segment that hides the probe sequence in the H conformation of a switch, T refers to a toggle segment that is present in certain molecular switches.

Embodiments of the invention relates to the design and application of bistable RNA and/or DNA constructs (A) that are switchable between two thermodynamically stable states. In preferred embodiments, the constructs are composed partially or entirely of mimetics of nucleic acids. One of the stable states includes a site for binding a target protein, nucleic acid, saccharide, small molecule, or supramolecular assembly. This binding site is sequestered in the second stable state. The detailed nature of the construct depends on the target. An example is provided for discovery of small molecules that inhibit the formation of a natural RNA-protein complex. A molecular switch with the desired properties is illustrated in a construct that tethers an all-DNA strand to an RNA-DNA chimeric strand. Other targets may bind natural RNA or DNA sequences, or the binding elements of the switch may be discovered via in vitro experiments to choose "combinatorially-derived sequence" molecules. The technology disclosed herein enables one skilled in nucleic acid chemistry and biophysical chemistry to design a suitable bistable construct and then to fine-tune the relative stability of the two forms.

Areas of Contemplated Use (1) Embodiments of the invention are directed to diagnostic tests for the presence of a protein, nucleic acid, supramolecular structure, whole or inactivated organism, or other ligand molecule (L) that binds preferentially to one of the two stable states of A. This stable state contains an analog of a naturally occurring RNA or DNA binding site for L (ligand binding domain).

(2) Embodiments of the invention are directed to the discovery of chemical entities (X) that interfere with binding of L to natural RNA or DNA analogs of A. One application involves X molecules that are leads for therapeutic agents against a disease state for which A-L interactions are necessary, e.g., interactions between SL3 of HIV-1 RNA and NCp7.

(3) Embodiments of the invention are directed to applications similar to (1), wherein the ligand binding domain of A comprises a combinatorially-derived sequence that is empirically chosen to bind tightly and specifically to L. Embodiments include field kits for real-time detection of infectious organisms or toxic agents.

(4) Embodiments of the invention are directed to applications similar to (2), wherein the ligand binding domain of A comprises a combinatorially-derived sequence that is empirically chosen to bind tightly and specifically to L. Embodiments include the discovery of chemical agents, X, for the remediation of effects due to infectious or toxic agents, L.

(5) Embodiments of the invention are directed to molecular electronic applications where the state change in A occurs in response to a triggering impulse, which may be a light pulse, that alters the state of a photosensitive ligand, L1, to L2. In these applications, the ligand binding domain of A may contain a natural RNA or DNA binding site for L1 or L2, or a combinatorially-derived sequence empirically chosen to bind tightly and specifically to either L1 or L2. The shape and properties of A will depend upon whether the combinatorially-derived sequence-binding pocket is occupied. Here, the construct may include a lumiphore quencher pair or other signal generating elements.

Embodiments of the invention rely on a conformationally bistable construction for A that is switched from one state (A1) to the other (A2) upon binding L. In the A2-L complex, the molecular conformation, A2, differs from that which predominates in the unbound state, A1. The state change may be detected by a change in luminescence, because the luminescent properties of A1 and A2 are designed to be very different. The fraction of A that is present as the A2-L complex is controlled by several thermodynamic factors, including (i) the relative affinity of L for A1 and A2, (ii) the A1/A2 equilibrium, and (iii) the input concentrations of the species. Some applications will include competitors, X, for the A2-L interaction, in which case the affinities of X for L, A1, and A2 are also relevant.

An embodiment of item (2), above, is used to illustrate the invention, where a bistable RNA/DNA construct including a lumiphore-quencher pair is disclosed for the rapid screening of agents to disrupt the SL3-NCp7 interaction in HIV-1. That embodiment is described in detail below. In that description, H, and O, replace the general nomenclature, A1 and A2, respectively.

Certain embodiments of the invention require the construction of an RNA and/or DNA (or other natural or nucleotide mimetic analogs) molecule that is switchable between two thermodynamically stable states. Illustrations and working examples are disclosed for double-hairpin constructs and cruciform structures.

HIV-1 has fifteen proteins and two identical RNA strands. Each of these is a potential target for drug interdiction. More details are given in several reviews and books (Frankel, A. D. and Young, J. A. T (1998) Ann. Rev. Biochem. 67:1-25; Coffin, J. M. et al. (1997) Retroviruses, Cold Spring Harbor Lab. Press, Plainview, N.Y.; Gallo, R. C., & Jay, G., eds. (1991) The Human Retroviruses, Academic Press, New York). Drugs currently in use target the viral reverse transcriptase (RT) and protease (PR). There are efforts to develop inhibitors of other HIV proteins. Several other HIV targets have been suggested. These include the nucleocapsid protein, as well as tat and rev (Frankel, A. D., and Young, J. A. T (1998) Ann. Rev. Biochem. 67:1-25).

Figure 1:
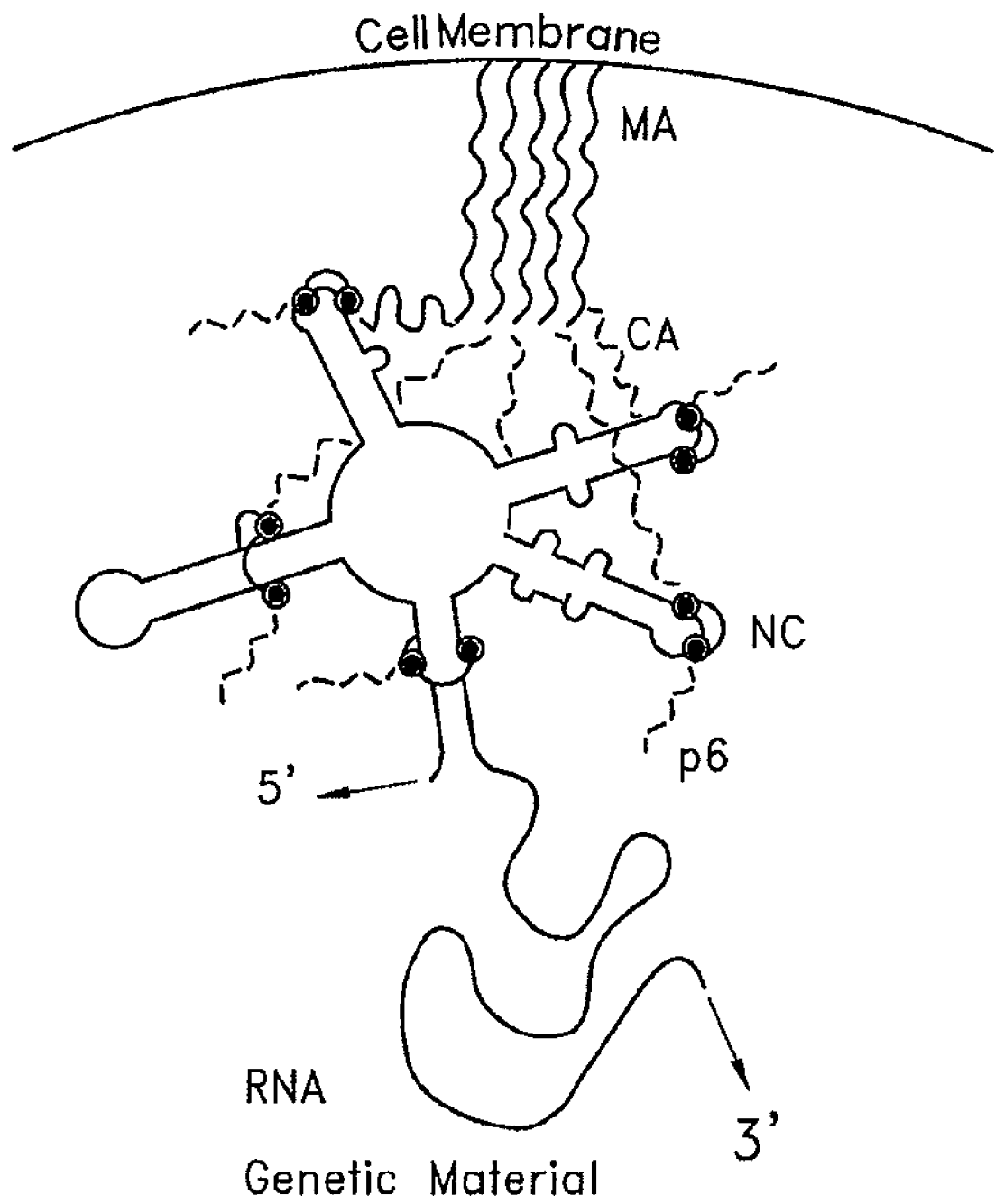
FIG. 1 is a schematic view of packaging in HIV-1 as a new virus particle assembles at the membrane of an infected cell. Each virus has two identical RNA strands, about 2000 gag and gag-pro-pol precursor proteins, and several other proteins and cellular components. As the virus matures, the precursors are processed into separate proteins, including NCp7. Within the precursor, the NC domains recognize sets of two loop G-residues ($G_2$ loci) in the RNA 5'-leader.

For HIV to reproduce, genomic RNA and viral proteins must form a "packaging complex," illustrated in FIG. 1. The 5'-leader region of the RNA contains sequences that allow only infectious RNA to be packaged into new virus particles, selected from the millions of other RNA molecules in a cell.

The NC domain or mature NCp7 has roles in packaging the RNA (Wills, J. W., & Craven, R. C. (1991) AIDS 5:639-654; Oertle, S, and Spahr, P. (1990) J. Virol. 64:5757-5763; Damgaard, C. K. et al. (1998) Nucleic Acids Res. 26:3667-76; DeGuzman, R. et al. (1998) Science 279:384-388), "chaperoning" functions (Williams, M. C. et al. (2001) Proc Natl Acad Sci USA 8:8), in refolding the RNA dimer in the virion (Fu, W. and Rein, A. (1994) J. Virol. 68:5013-5018), and annealing the primer tRNA onto the genomic RNA for reverse transcription (Prats, A. C. et al. (1988) EMBO J. 7:1777-1783). It also interacts with viral proteins including reverse transcriptase (Druillennec, S. et al. (1999) J. Biol. Chem. 274:11283-8; Lener, D. et al. (1998) J. Biol. Chem. 273:33781-6), and the accessory protein, Vpr, to play a role in stable integration of the proviral DNA in the chromosomes of infected cells (de Rocquigny, H. et al. (2000) Eur. J. Biochem. 267:3654-60). Thus, drugs that target the nucleocapsid protein and/or its interactions with other HIV-1 molecules have the potential to interfere with critical functions at many stages of the viral life cycle (Darlix, J. L. et al. (2000) Adv. Pharmacol. 48:345-72; Berthoux L. et al. (1999) J. Virol 73:10000-9).

The NC, tat, and rev proteins all interact with RNA in regions that can be created with the luminescent RNA/DNA chimeras in accordance with preferred embodiments of the present invention, as described below in greater detail. Thus, those of ordinary skill in the art will appreciate that the compositions and methods used to screen anti-NC candidates disclosed herein can be readily adapted for these other HIV-1 targets, as well as molecular targets in other disease states, or to detect the presence of a protein, organism, toxin, or other target.

Anti-NC Strategies

A goal of targeting an enzyme with an equilibrium-binding agent is to decrease the enzyme's turnover rate. Small changes in the binding free energy of competitors may be amplified by exponential decreases in turnover. Thus, drugs having micromolar or even millimolar affinities may be sufficiently effective as long as Absorption, Distribution, Metabolism, Elimination, Toxicity ("ADME/Tox") properties are favorable. This is the fundamental advantage in targeting RT, PR, or IN over viral substances that exert their influence by mass action. On the other hand, this amplifier effect confers a strong survival advantage on mutants resistant to a drug. In a short time, a mutant strain can dominate an infection.

The mature NCp7 protein presumably turns over in its chaperoning activity. Thus, it is possible there will be an amplifier effect similar to that for equilibrium binding drugs to inhibit RT, PR, or IN. The packaging function of NC, however, seems to be dominated by mass action—2000 gag precursor proteins are available to recognize the packaging domain RNA for each virus. An answer to mass action is tighter binding. Thus, the preferred target drugs will exhibit high affinity binding to the HIV-1 RNA.

A possible way to skirt problems due to low affinity or a mass-action function is for a drug to covalently inactivate the target. There have been attempts to adapt sulfur-reactive compounds to attack cysteine side chains in the zinc fingers (Rice W G et al. (1993) Nature 361:473-5; Rice W G et al. (1995) Science 270:1194-7; Chertova E N et al. (1998) Biochemistry 37:17890-7; Huang M et al. (1998) J Med. Chem. 41:1371-81; Guo J et al. (2002) J. Virol. 76:4370-8; Yovandich J L et al. (2001) J. Virol. 75:115-24; Berthoux, L et al. (1999) J Virol 73:10000-9). Cys49, in the C-terminal finger (FIG. 2), reacts fastest with N-ethylmaleimide (NEM) in vitro (Chertova E N et al. (1998) Biochemistry 37:17890-7). A cascade of reactions then ejects $Zn^{2+}$ from both fingers. The reaction with NEM is slow even at relatively high concentrations (~8 mM NCp7, 50 mM NEM; $t_{1/2} \cong 30$ min for forming the C49 adduct).

Other "zinc-ejecting" alkylating agents have been tested (Rice W G et al. (1993) Nature 361:473-5; Rice W G et al. (1995) Science 270:1194-7; Chertova E N et al. (1998) Biochemistry 37:17890-7; Huang M et al. (1998) J Med. Chem.

41:1371-81; Guo J et al. (2002) *J. Virol.* 76:4370-8; Yovandich J L et al. (2001) *J. Virol.* 75:115-24; Berthoux, L et al. (1999) *J Virol* 73:10000-9). However, cysteines are common, as are zinc-chelating proteins. Thus, zinc ejection seems to violate the principle that one should attack HIV at processes that are specific to the virus.

In an attempt to counter this concern, some reagents were tested with zinc-containing transcription factors. The experimenters suggested that the reagents were selective for reaction with NC, while the cysteines chelating zinc in the fingers of the transcription factors were not alkylated. However, examination of the protocol (Huang M et al. (1998) *J Med. Chem.* 41:1371-81) shows that the latter reaction was conducted in the presence of the DNA substrate for the cellular protein. Alkylation of Cys49 can be stopped almost completely by preincubating NCp7 with $d(GT)_n$ oligomers in 2-fold excess (Chertova E N et al. (1998) *Biochemistry* 37:17890-7); these bind much more weakly than the natural RNA substrates for NC (see EXAMPLES). Selectivity then remains an open question. It is likely that both NC and cellular transcription factors are present mostly as RNA or DNA-bound forms.

Others have experimented with short single-stranded DNA molecules (Vuilleumier, C et al. (1999) *Biochemistry* 38:16816-25; Mely, Y et al. (1994) *Biochemistry* 33:12085-91; Maki, A. H. et al. (2001) *Biochemistry* 40:1403-1412; Fisher, R. J. et al. (1998) *J Virol* 72:1902-9), or DNA and NC mimetics (Druillennec S et al. (1999) *Bioorg Med Chem. Lett.* 9:627-32; Druillennec S et al. (1999) *Proc Natl Acad Sci USA.* 96:4886-91). The $K_d$ values are probably in the millimolar range at best, although this is difficult to confirm.

In work on deoxy dinucleotides where the phosphodiester was replaced by a methylene carboxamide linker (Druillennec S et al. (1999) *Bioorg Med Chem. Lett.* 9:627-32), $K_d$ values for NC binding were estimated at 6 µM for TG, 100 µM for GT, and >1000 µM for TT. Protein binding for the dinucleotides is considerably weaker than for SL3 or SL2 RNA, but it is encouraging that uncharged molecules with MW ~500 exhibit both affinity and sequence specificity. The other conclusions are that the TG molecule: (i) penetrates cells in an HIV-1 infected cell line, (ii) inhibits RT activity by 20% at a concentration of 10 µM, and (iii) appears to snap NC into the same binding conformation given that shifts in the NMR spectrum of NC are similar to those induced by longer nucleic acids.

A cyclic peptide that competes with NC for in vitro recognition of its RNA, DNA and protein targets may function as a mimic for NC (Druillennec, S et al. (1999) *Proc Natl Acad Sci USA* 96:4886-91). This hexapeptide, c(F-C-dW-R-C-K), has strong structural similarities in the locations of W, F, and basic side chains in NCp7. It also exhibits In vivo effects that suggest impairment of proviral DNA synthesis, perhaps by direct interaction with RT or by interfering with annealing the tRNA primer to genomic RNA.

There is also some enthusiasm for competitive inhibitors based on RNA aptamers that have been created with nanomolar affinities for NCp7 (Lochrie, M. A. et al. (1997) *Nucleic Acids Res* 25:2902-10; Berglund, J. A. et al. (1997) *Nucleic Acids Res* 25:1042-9; Allen, P. et al. (1996) *Virology* 225:306-15). Most of the binding studies were conducted at low salt and the stoichiometry was not clearly established. Therefore, some of these molecules are considered as possible candidates herein. However, unmodified DNA and RNA molecules may not readily pass the cell membrane and survive long enough in a cell to disrupt the target NC-RNA interaction.

The present screening methods are applicable for the high-throughput assay of low-molecular weight lead compounds. Generally, low-MW drugs are more permeable to cell membranes than macromolecules, are accessible by organic synthesis, and pharmaceutical companies are experienced in formulating similar compounds for oral dosage. Libraries of thousands of "drug-like" compounds are now available for high throughput screening. They possess diverse molecular scaffolds to locate lead compounds, which can be modified by combinatorial and rational design to optimize their NC affinity, and ADME/Tox properties.

The compounds and methods disclosed with respect to the NC-RNA system should be directly applicable for developing and testing useful low-MW compounds. Indeed, the work in measuring affinities, in structure determination by NMR, and stabilizing NCp7 against denaturation, disclosed herein, can be applied in a vigorous program of anti-nucleocapsid drug discovery and design.

Structural Biology of Packaging

Figure 3:
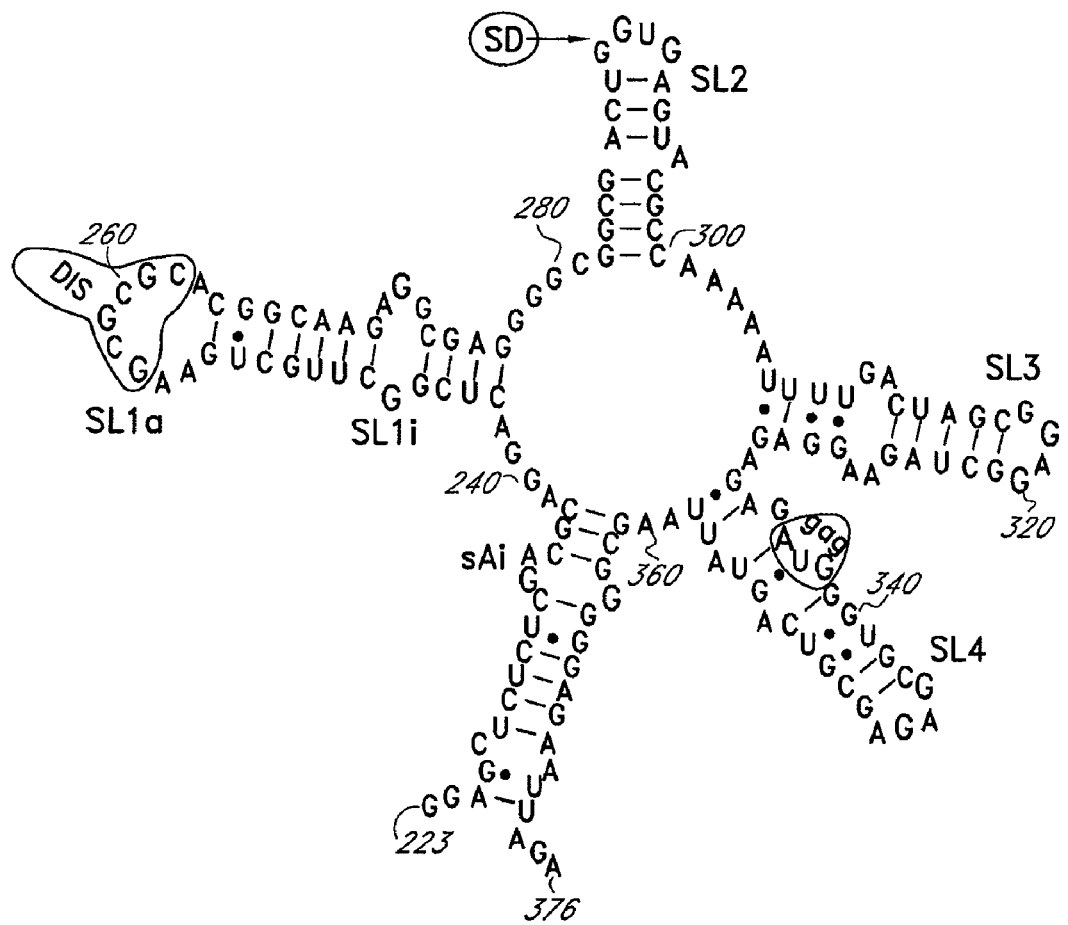
FIG. 3 is a hypothetical secondary structure of the HIV-1 RNA domain near the 5'-major splice donor (SD) (SEQ ID NO: 9) (Pappalardo, L. et al. (1998) *J. Mol. Biol.* 282:801-818). Several known and potential $G_2$-loci are noted.

FIG. 3 shows a plausible secondary folding of the major packaging domain of HIV-1 RNA. Several elements for controlling the viral life cycle are contained within this ~150 nucleotide sequence. (1) A metastable RNA dimer forms around the dimer initiation sequence (DIS) (Muriaux, D. et al. (1996) *Biochemistry* 35:5075-82; Muriaux, D. et al. (1996) *J Biol Chem* 271:33686-92; Clever, J. L. et al. (1996) *J. Virol.* 70:5902-8; Laughrea, M. et al. (2001) *Virology* 281:109-116) in SL1, which then matures in the virion to a more stable form condensed with NCp7 (Fu, W. & Rein, A. (1994) *J. Virol.* 68:5013-5018). The mature virus has about one NCp7 per 10-12 nucleotides. (2) The 5'-major splice donor (SD) in SL2 is a primary RNA processing site. Since spliced mRNA is not packaged, it is likely that packaging determinants reside in the sequence or folded structure of the region near SD. (3) A determinant of packaging is SL3, in which two nearby guanine residues ($G_2$-loci) appear to be involved in specificity; $G_2$-loci in other stem-loops are also involved. The following paragraphs give a more complete description of the background to packaging. (4) The coding region for the gag genes begins in SL4.

Many details of packaging in retroviruses have come into focus (Coffin, J. M. et al. (1997) *Retroviruses*, Cold Spring Harbor Lab. Press, Plainview, N.Y.; Gallo, R. C., & Jay, G., eds. (1991) *The Human Retroviruses*, Academic Press, New York; Clever, J. L. et al. (1999) *J. Virol.* 73:101-9; Clever, J. L. & Parslow, T. G. (1997) *J. Virol.* 71:3407-14; McBride, M. S. & Panganiban, A. T. (1996) *J. Virol.* 70:2963-73; McBride, M. S. et al. (1997) *J. Virol.* 71:4544-54; Clever, J. et al. (1995) *J Virol* 69:2101-9). In HIV-1 about 1500-2500 polyprotein precursors (pr-gag, and pr-gag-pol) assemble at the inner membrane of the forming virion (Vogt, V. M. & Simon, M. N. (1999) *J Virol* 73:7050-5) rather than just the few illustrated in FIG. 1. Each of these proteins contains a nucleocapsid domain that is required for packaging to occur. The 55 kD gag precursor polyprotein is later processed by the viral protease to "structural" proteins, including NCp7 (Linial, M., & Miller, A. D. (1990) *Curr. Top. Microbiol. Immunol.* 157:125-152; Gelderblom, H. R. (1991) *AIDS* 5:617-638). NC-domains within gag precursors bind to the RNA with several RNA-NC interactions responsible for full discrimination of genomic from non-genomic RNA (Clever, J. L. et al. (1999) *J. Virol.* 73:101-9; Clever, J. L. & Parslow, T. G. (1997) *J. Virol.* 71:3407-14; McBride, M. S. & Panganiban, A. T. (1996) *J. Virol.* 70:2963-73; McBride, M. S. et al. (1997) *J. Virol.* 71:4544-54; Clever, J. et al. (1995) *J Virol* 69:2101-9). The NC-domains interact via a conserved zinc finger motif (FIG. 2). Mutants of the fingers that render them incompetent for zinc binding destroy the capacity to recognize and package genomic RNA (Aldovini, A. & Young, R. A. (1990) *J Virol* 64:1920-6; Gorelick, R. J. et al. (1988) *Proc Natl Acad Sci USA* 85:8420-4; Dupraz, P. et al. (1990) *J Virol* 64:4978-87). It is thought that interactions with the two fingers in NCp7 are the same as in the precursor.

Most HIV-1 packaging specificity occurs with sequences encompassed by the nucleotides shown in FIG. 3 (Pappalardo, L. et al. (1998) in *Structure, Motion, Interaction and Expression of Biological Macromolecules*, pp. 125-135 (R. H. Sarma & M. H. Sarma, eds.); Shubsda, M. F. et al. (2002) *Biochemistry* 41:5276-82). There have also been measurements of the association constants of various RNA fragments with the 15 kDa NCp7 precursor protein (Clever, J. et al. (1995) *J Virol* 69:2101-9), and GST-NC fusion proteins (McBride, M. S. & Panganiban, A. T. (1996) *J. Virol.* 70:2963-73) indicating that all four hairpins are involved with NC-domain interactions. Each loop is a favorable candidate for interaction with the NCp7 zinc-finger domain, with 2 or 3 G residues in single-stranded loops; G may be a requirement for interaction with the finger in the native RNA sequence (South, T. L. & Summers, M. F. (1993) *Protein Sci* 2:3-19; Summers, M. F. et al. (1992) *Protein Sci*, 1:563-574; Delahunty, M. D. et al. (1992) *Biochemistry* 31:6461-6469). Removal of SL3 reduces packaging efficiency by ~90%, but does not completely eliminate packaging (Clever, J. L. & Parslow, T. G. (1997) *J. Virol.* 71:3407-14). This suggests that RNA-NC domain interactions may occur at several sites to provide full specificity.

Figure 4:
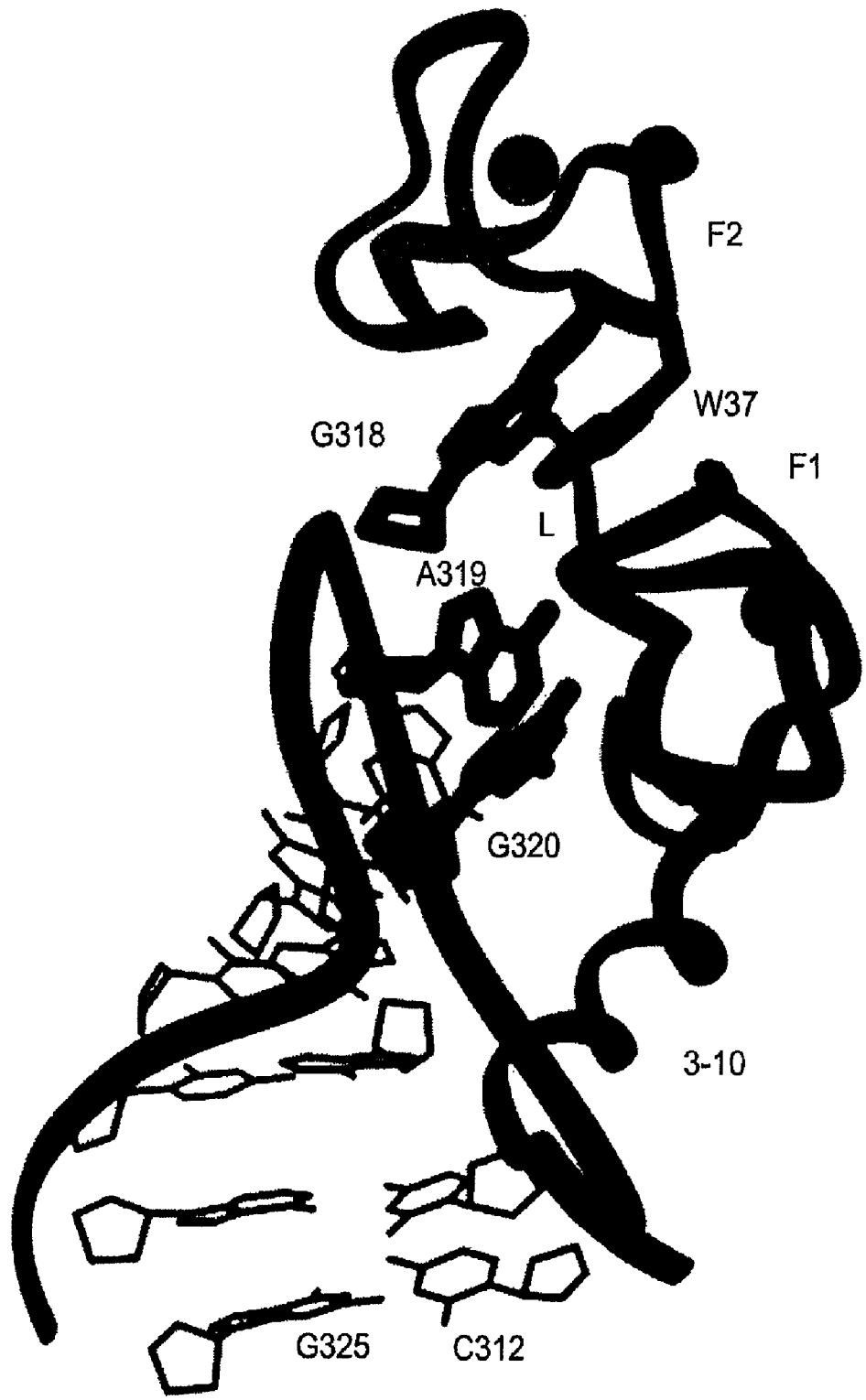
FIG. 4 is a detailed view of part of the packaging signal interaction, showing the SL3-NCp7 complex (DeGuzman, R. et al. (1998) *Science* 279:384-388). It can be seen that W37 of the protein stacks on G318.

A high-resolution view of a packaging signal complex is illustrated in FIG. 4 (DeGuzman, R. et al. (1998) *Science* 279:384-388; Pappalardo, L. et al. (1998) *J. Mol. Biol.* 282:801-818). FIG. 4 shows the complex between a 20mer SL3 construct and the 55mer NCp7. No NMR or x-ray structures for complete retroviral packaging signals have been reported, although there are several other structures for substantial subsets (Amarasinghe, G. K. et al. (2000) *J. Mol. Biol.* 299:145-156; Amarasinghe, G. K. et al. (2000) *J. Mol. Biol.* 301:491-511; Kerwood, D. J. et al. (2001) *Biochemistry* 40:14518-29; Mujeeb, A. et al. (1998) *Nat Struct Biol* 5:432-436; Takahashi, K. I. et al. (2000) *RNA* 6:96-102; Theilleux-Delalande, V. et al. (2000) *Eur J Biochem* 267:2711-2719; Ennifar E et al. (2001) *Nat Struct Biol.* 8:1064-8; Zeffman, A. et al. (2000) *J. Mol. Biol.* 297:877-93; Morellet, N. et al. (1998) *J. Mol. Biol.* 283:419-34). There is a high degree of similarity of the interactions between NCp7 and nucleic acid in these complexes. Thus it is likely that the development and testing of anti-nucleocapsid drugs can be guided by molecular modeling based on the conserved structure.

FIG. 3 shows that splicing would destroy this secondary structure (SD is at 289-290), removing essential portions of SL2 and sA as well as all of SL3 and SL4. That provides a natural explanation for the selection of unspliced RNA for packaging. We have examined about 500 sequences in Genbank containing SL3, and found (Lin, Y. (2002) Ph.D. Thesis, Syracuse University; "Database and Algorithmic Applications in Nucleic Acid Sequence, Structure and NMR Frequencies, and in Efficient Chemical Depiction."; which is incorporated herein in its entirety by reference) that only the first and third base in the GGAG tetraloop of SL3 vary more than twice (about the rate of sequencing errors). The $G_2$-locus at 318 and 320, which is involved in the specific complex of FIG. 4, may be required for a functioning virus. G317A mutants do occur rarely, but it is predicted that A317 will stack on the stem in the same fashion as G317. Further, there are very few non-conservative variations in the NC domain. Thus, targeting the NC-SL3 interaction for drug interdiction holds special promise in the inability of the virus to escape anti-NC drugs by mutation.

EXAMPLES

Example 1

Affinities of RNA Loops for NCp7

In spite of progress in defining the packaging signal, we have characterized the stoichiometry and affinity of NC proteins for the RNA stem-loops only recently (Shubsda, M. F. et al. (2002) *Biochemistry* 41:5276-82). Part of the problem was that most early studies neglected the salt dependence of the interaction between the highly charged components (NCp7 has a charge of +9 at neutral pH, and RNA has one negative charge per phosphate). Using an ionic strength of 0.2 M reduced non-specific binding and led to full quenching of Trp-37 fluorescence, a 1:1 stoichiometry for each of the component stem-loops in the major packaging domain (Shubsda, M. F. et al. (2002) *Biochemistry* 41:5276-82; FIG. 3), and gave results consistent with NMR-based structures of SL3 and SL2 complexes (DeGuzman, R. et al. (1998) *Science* 279:384-388; Amarasinghe, G. K. et al. (2000) *J. Mol. Biol.* 299:145-156; Amarasinghe, G. K. et al. (2000) *J. Mol. Biol.* 301:491-511). We found that non-specific interactions contributed heavily to the binding at low ionic strength where most previous studies had been done (0.2 M NaCl is near physiological conditions; in blood the ionic strength is ~0.18 M ignoring contributions of charged macromolecules; Kratz, A. & Lewandrowski, K. (1998) *New Eng. J. Med.* 339:1063-1072).

Figure 5:
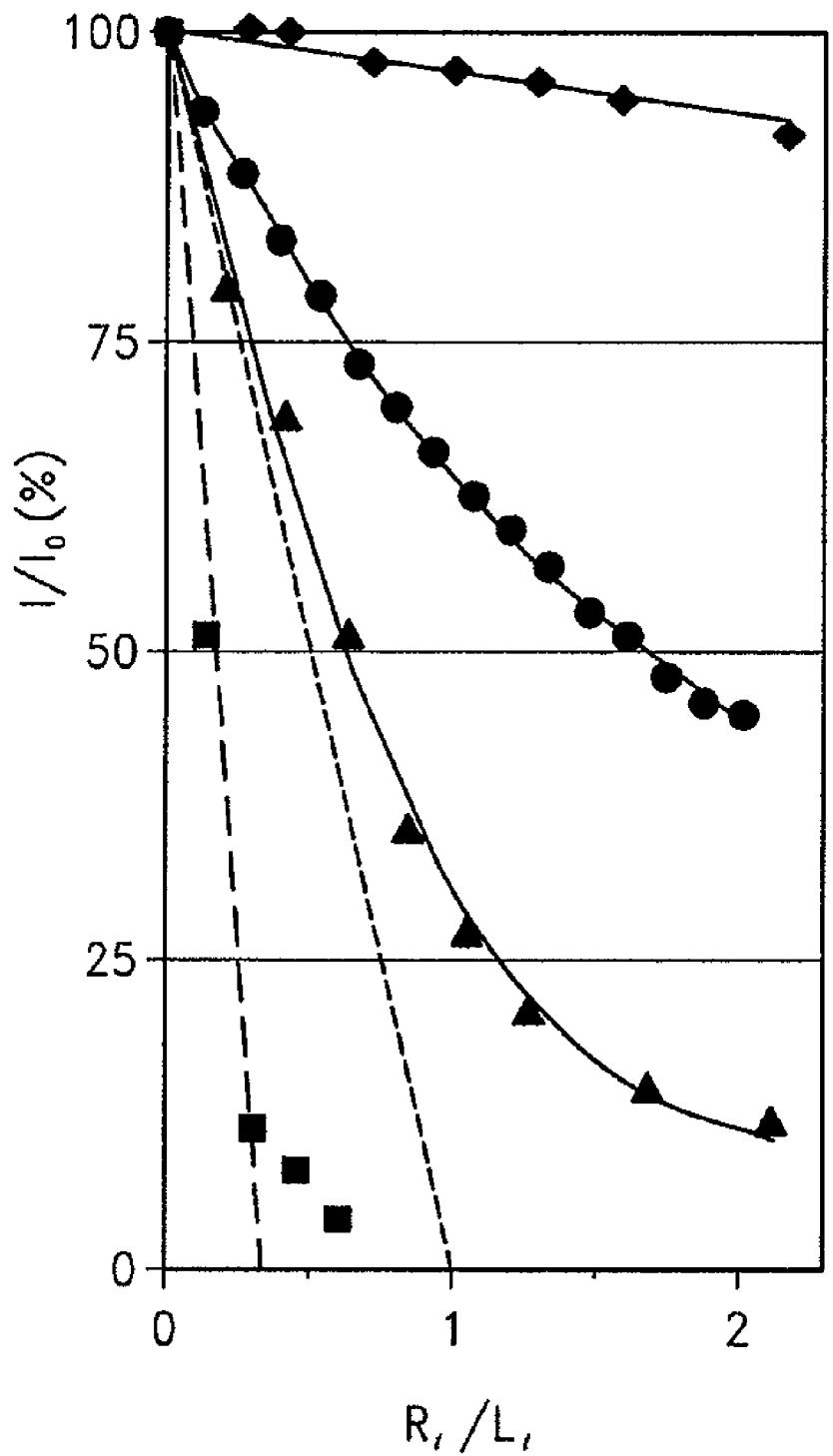
FIG. 5 illustrates quenching W37 in NCp7 by four HIV-RNA molecules. ♦ SL3-UUCG, ● SL4, ▲ SL3, ■ 154mer full domain; solid lines represent calculated fits for 1:1 complexes (see text). Short dashed line: ideal $R_1L_1$ complex, long dashes: ideal $R_1L_3$ complex. $R_t$ and $L_t$ are the total concentrations of RNA and ligand (NCp7), respectively.

We found that the $G_2$-loci noted in FIG. 3 are indeed sites for interaction with NCp7. They form complexes that have dissociation constants, $K_d$=20-300 nM at 0.2 M NaCl (Shubsda, M. F. et al. (2002) *Biochemistry* 41:5276-82). Variations in affinity occur among the loop sequences, with SL3 and SL2 binding most tightly (See Table 1 for selected $K_d$ values and FIG. 3 for the loop definitions). The binding constants are derived from a tryptophan fluorescence assay illustrated in FIG. 5 (hereinafter, "Trp assay", "Trp-binding assay", or similar variations).

TABLE 1

Dissociation constant and relative affinity for RNA-NCp7 complexes.

| RNA | $K_d$ (nM) | RA[a] |
|---|---|---|
| SL1a | 100 ± 10 | 28% |
| SL1i | 140 ± 20 | 20% |
| SL2 | 23 ± 2 | 120% |
| SL3 | 28 ± 3 | 100% |
| SL4 | 320 ± 30 | 9% |
| SL3-UUCG | ~7,500 | 0.4% |
| SL3-GAUA | ~16,000 | 0.2% |
| SL3-GGUG | 10 ± 2 | 280% |
| SL3-all-DNA | 230 | 12% |
| SL3-(DNA stem)-(RNA loop) | 30 | 100% |

[a]Affinity for NCp7 relative to SL3.

The assay is based on quenching of the fluorescence of tryptophan-37 in the protein by residues in the single-stranded RNA loops. The G318/W37 stacking in the SL3-NCp7 structure is illustrated in FIG. 4. Tightly bound RNA molecules quenched nearly all the fluorescence of NCp7 in 0.2 M NaCl. The tightest binding variant we have examined (Paoletti, A. C.; Shubsda, M. F.; Hudson, B. S.; Borer, P. N.

(2002) *Biochemistry* 41, 15423-15428; "Affinities of the HIV-1 Nucleocapsid Protein for Variants of SL3 RNA."; incorporated in its entirety by reference thereto), SL3-GGUG, has a limiting fluorescence that plateaus at the background of the buffer (A319 is changed to U in this variant, see FIG. 3). Its binding profile approached that of a 1:1 complex with an infinite binding constant ($1K_d$; similar to the short-dashed line in FIG. 5). In contrast, when the GGAG-tetraloop of tight-binding SL3 is replaced with UUCG or GAUA, quenching was almost nil indicating very low affinity. This is consistent with the primary event in W37 quenching being the close stacking of G318. In addition, there are primarily electrostatic interactions between the N-terminal 3-10 helix and the RNA stem (see FIG. 4). The binding site covers a substantial part of this small protein's surface.

A 154mer construct (the entire sequence in FIG. 3 that includes all four stem-loops; SEQ ID NO: 9) bound tightly to NCp7. The assay indicated that the equivalent of three NCp7 molecules were bound with high affinity per RNA (see FIG. 5, where the binding isotherm intersects the axis at $R_t/L_t \cong 0.33$; it is possible that two strong sites and several weaker ones combine to give the appearance of three strong sites). This is the first evidence that multiple NC-interactions are likely to occur with the 5'-leader.

All but one of the earlier studies of stoichiometry and affinity were performed at ionic strengths below 0.2 M (Damgaard, C. K. et al. (1998) *Nucleic Acids Res* 26:3667-76; Shubsda, M. et al. (1999) *Biophys Chem* 76:95-115; Shubsda M. F. et al. (1999) *Biochemistry* 38:10147-57; Shubsda, M. F. et al. (2000) *Biophys. Chem.* 87:149-65; McPike, M. P. et al. (2001) *Biochemistry*; Amarasinghe, G. K. et al. (2001) *J Mol Biol* 314:961-970; Berglund, J. A. et al. (1997) *Nucleic Acids Res* 25:1042-9). However, we found unusual properties in the system at low ionic strength. This included irreproducibility of the binding isotherms, decreases in the initial fluorescence, increases in the residual fluorescence, and binding curves that can only be described by at least two binding constants. The low-salt regime appears to be dominated by nonspecific interactions between these highly charged molecules; the free protein may also be less structured at low salt. By contrast, SL3 titrations at 0.2 M NaCl (FIG. 5) were highly reproducible. The $K_d$ for SL3 in Table 1 is the average of 11 determinations with six different protein preparations (standard deviation <10%).

We found a linear salt dependence at 0.2-0.8 M NaCl (Shubsda, M. F. et al. (2002) *Biochemistry* 41:5276-82), and estimated that there are five to six ion pairs in the SL3-NCp7 complex. In agreement, the NMR structure predicts six salt-bridge interactions between basic side-chains of the protein and the RNA phosphates (DeGuzman, R. et al. (1998) *Science* 279:384-388).

SL3 variants and modified RNAs We have studied the sequence dependence of binding in about 50 variants of SL3 (Paoletti, A. C.; Shubsda, M. F.; Hudson, B. S.; Borer, P. N. (2002) *Biochemistry* 41, 15423-15428). There are 64 possible variants of the loop positions GXYZ using A, C, G, U (the first G-residue was held constant as it is not involved in the loop-NC interaction). Strong binding occurred when XYZ=GNG, but the other loop sequences were considerably weaker. Interestingly, the preferred sequence for greater affinity was that Z=G; this corresponds to G320, and is not the base that stacks on W37 (FIG. 4). A DNA 20mer version of SL3 had about 15% of the affinity of SL3 RNA.

Several changes are tolerated in the sequence that are useful in designing the luminescence-quenching pair RNA/DNA chimeric switches of the present invention, or in designing test competitors with reduced complementarity to the switches (Paoletti, A. C.; Shubsda, M. F.; Hudson, B. S.; Borer, P. N. (2002) *Biochemistry* 41, 15423-15428). For instance, a 16mer RNA construct was found to bind NCp7 with the same affinity as the 20mer used in earlier studies (Shubsda, M. F. et al. (2002) *Biochemistry* 41:5276-82), and only the loop needs to be RNA for efficient binding (see last entry in Table 1). There was virtually no change in $K_d$ upon substituting base pairs near the loop, C316-G321→G316-C321, G315-C322→(C315-G321 or A315-U322). Also, G320→dG320 was well tolerated, and only slight reduction in affinity was engendered by substituting inosine at loop sites 317, 318, or 320.

We also studied several nucleotide DNA oligomers containing the G-X-G sequence. These have been reported (Vuilleumier, C. et al. (1999) *Biochemistry* 38:16816-25; Fisher, R. J. et al. (1998) *J Virol* 72:1902-9) to possess relatively high-affinity for NCp7. However, none of these molecules had even micromolar affinity for NCp7 at 0.2 M NaCl (Paoletti, A. C.; Shubsda, M. F.; Hudson, B. S.; Borer, P. N. (2002) *Biochemistry* 41, 15423-15428).

We mapped the affinities of the wild-type interaction sites for NCp7 in the major packaging domain of the 5'-leader RNA (Shubsda, M. F. et al. (2002) *Biochemistry* 41:5276-82), and explored the diversity of interactions using variants of the SL3 loop. In order to design and evaluate anti-NC drugs it is useful to know the affinities the protein has for its natural substrates under physiological conditions, and to probe the nature of binding loci by systematic variation of the sequence. The results add to our understanding of RNA-protein interactions, highlighting problems that may occur when these studies are conducted at low ionic strength. We also demonstrated that multiple NCp7 proteins interacted with the major packaging domain, and that a linear G-X-G loop sequence in the RNA was not required for high affinity. A close correlation was found to exist between structural features and our rapid technique to evaluate the diversity of RNA-NC interactions.

The Trp-binding assay provided a reliable method to establish structure/free energy relationships. The simple expedient of comparing affinities at 0.2 M NaCl is sufficient to distinguish trends that are helpful in designing anti-NC agents. However, significant obstacles prevent use of the Trp-assay as a high throughput screen. (1) It is not sensitive enough to accurately measure the affinities of tight-binding complexes, where low concentrations are required for appreciable dissociation of the complex. (2) The Trp assay requires fluorescence excitation in the UV, which will restrict its application in high-throughput screening of anti-NC drug candidates. (3) A Trp-based assay is inherently less sensitive than one using dyes for labeling proteins and nucleic acids with lumiphores that absorb and emit in the visible region of the spectrum.

High-Resolution Structures

The structure of a relevant complex is an extremely valuable guide in undertaking drug-design. The structure for the NCp7-SL3 complex is presented in FIG. 4. G318 interacts in a hydrophobic cleft of F2, the upper zinc finger shown in the figure and a very similar interaction is made between G320 and F1. These two residues comprise the $G_2$-locus for the SL3 loop, and each G-base makes identical H-bonds with backbone amides and carbonyls in the fingers. Electrostatic interactions also play a role because of the high formal charges involved, +9 for $Zn_2.NCp7$ and −19 for the SL3 20mer. The electrostatic surface of the protein (not shown) has the RNA in a deep electropositive pocket on the nucleotide-binding surface of the protein. We also used NMR to determine the structure of the unbound RNA, which alters considerably upon binding the protein (Pappalardo, L. et al. (1998) *J. Mol. Biol.* 282:801-818). The structures of the finger domains are largely determined by coordination to the zinc, and do not change upon binding RNA or DNA. However, the linker and the termini are flexible in the absence of nucleic acid at low ionic strength (Lee, B. M. et al. (1998) *J. Mol. Biol.* 279:633-49). The N-terminal residues form a 3-10 helix in the complexes with SL3 and SL2; this helix interacts mainly by salt-bridge interactions with the RNA stem.

High-Throughput Assays

Our work on the RNA-NC complex is relevant to the design of high-throughput drug discovery. We have established reliable assay conditions, and describe a multiplex assay to examine many thousands of potential inhibitors. We also have completed a survey of the affinities of the most important wild-type RNA substrates for NC binding, and have explored the diversity of interactions (Table 1). We have high-resolution structures to guide our search for anti-NC agents.

The design of high-sensitivity and high-throughput assays take advantage of our earlier work on the SL3-NCp7 system. The detection scheme uses highly efficient fluorophore labels similar to known molecular beacons (Tyagi, S. & Kramer, F. R. (1996) *Nat Biotechnol* 14:303-8; Fang, X. et al. (2000) *Anal Chem* 72:747A-753A). The beacons utilize the process called Fluorescence Resonance Energy Transfer (hereinafter "FRET").

Example 2

Unimolecular Biostable Nucleic Acid Switch

Figure 6:
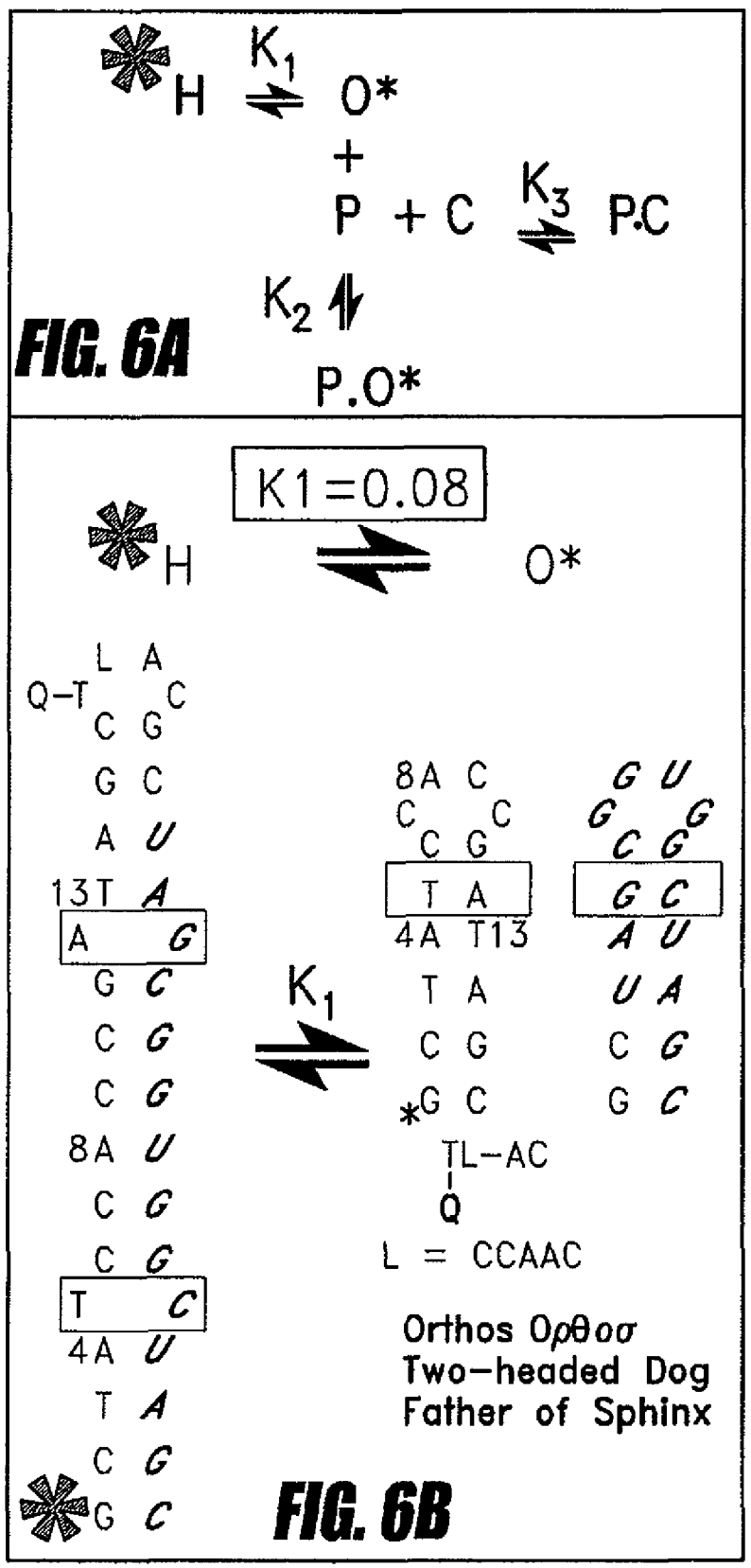
FIG. 6. (a) Equilibria for complex formation between a protein, P, competitor, C, and a nucleic acid switch. (b) The "C3" sequence (SEQ ID NO: 7) used in phase I is shown, with the H-form at the left and O-form at the right. DNA is shown in red and RNA in blue, gray blocks designate base pairs in O that are lost in H, the high affinity GUG sequence is in the blue oval, * is a fluorescein derivative, 6-hydroxy fluorescein (FAM), and Q is the fluorescence quencher, Dabsyl that replaces the 5-methyl of T.

The principles of the unimolecular bistable OrthoSwitches are illustrated in FIG. 6 and SEQ ID NO: 7. The DNA part of the sequence (shown in red) was designed to make the "H" state be more stable than the two-headed "O" state. The high affinity NC-binding sequence, GUG, is located in an RNA tetraloop in the O-form. The DNA sequence was engineered to set the equilibrium constant, K1, between 0.01 to 0.1 and, as shown below, it is 0.08. This simply means that the ratio of concentrations, [O]/[H]=0.08. A fluorophore is placed at the 5'-end of the chain (*), and a quencher at the location marked Q. The distance between fluorophore and quencher is much larger in H than in O, so H has much stronger fluorescence. Such "molecular beacons" operate on the principle of FRET. The efficiency of transfer increases as the inverse sixth quencher. Thus a small change in distance between the dyes can lead to a large change in fluorescence.

The scheme in FIG. 6a is now easily understood. The K1 equilibrium favors the "bright" H-form in the absence of NC protein, P. However, increasing [P] will cause it to bind GUG, consuming O. As more P is added, H is consumed to produce more of the "dark" P·O complex. However, a drug candidate, C, that binds strongly to P will displace O, which reverts to the bright H-form. A multiwell format for high throughput screening would be to put identical amounts of switch and protein in each well, then to add a different candidate to each. The wells that are brightly fluorescent contain promising drug leads with substantial affinity for the protein target.

Figure 7:
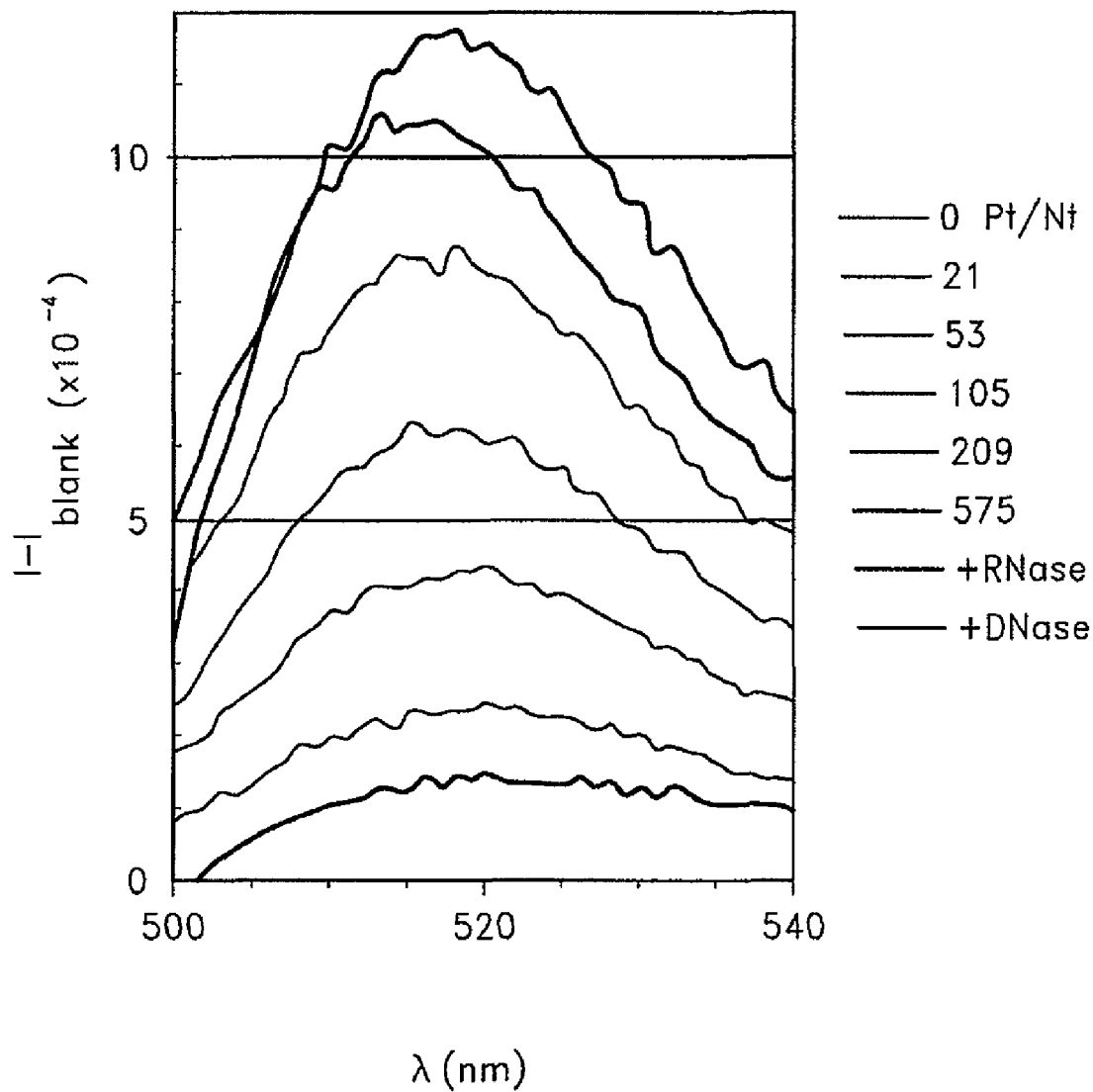
FIG. 7. Fluorescence of the C3 (SEQ ID NO: 7) (heavy blue line, second from the top, at concentration, $N_t$=10 nM). Additions of NCp7 are shown in light lines (21 to 575 molar equivalents of protein). The heavy red line (bottom) is for the $P_t/N_t$=575 sample treated with RNase, and the heavy green line (top) is for that sample treated with DNase.
Figure 8:
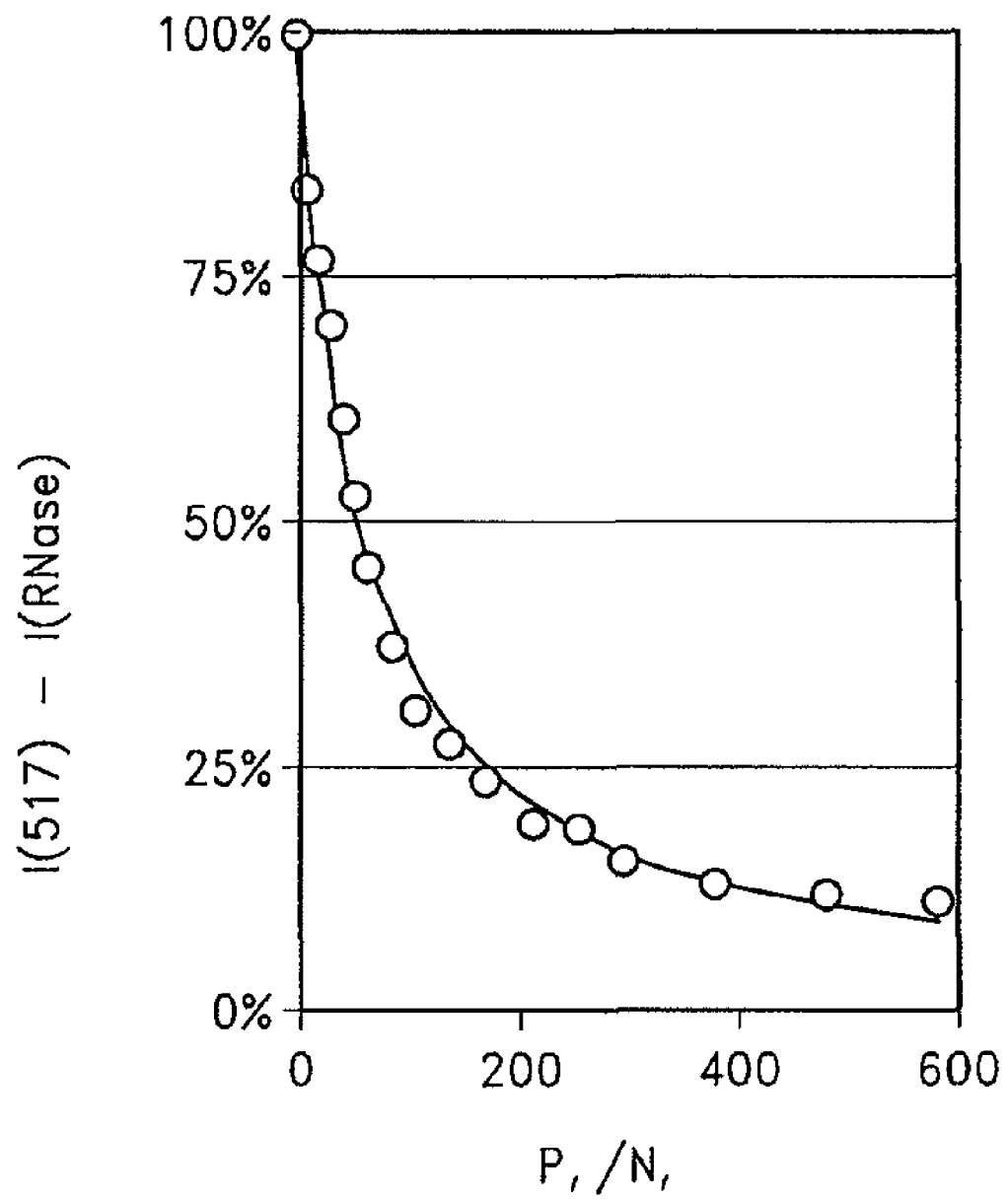
FIG. 8. FRET-monitored titration of the C3 (SEQ ID NO: 7) ($N_t \cong 10$ nM). [NCp7] increases left to right, expressed as the ratio $P_t/N_t$. The emission at 517 nM is reported after subtracting that of the RNase treated sample. The fit uses a single binding constant $K_d^1$=500 Nm. Uncertainty in $N_t$ limits the precision of this determination.

Tests show the system works as planned. The fluorescence decreases as NC is added, and a minimum fluorescence for the O-form can be established by adding ribonuclease. These features are clearly seen in FIG. 7. The heavy blue curve shows the fluorescence emission spectrum of a 10 nM solution of C3 (SEQ ID NO: 7). Increasing amounts of NC were added, resulting in a rapid decrease in fluorescence as the H-form is consumed to make the P·O complex. This titration with more data points is shown in FIG. 8.

Example 3

Screening for NC Inhibitors

The NC/switch complex is capable of identifying a high affinity inhibitor of NC by generating an optical signal. This requires the protein bound "dark" switch to dissociate in the presence of a high affinity NC inhibitor, producing an unbound "bright" switch.

In this experiment, SL2 from the HIV-1 packaging domain was used. It has a high affinity for NC ($K_d$=25 nM) and is not predicted to bind to any part of the switch at the concentrations used. SL2 also has GUG in the loop, similar to the O-form of the NC-Switch, but has a very different stem sequence.

Figure 9:
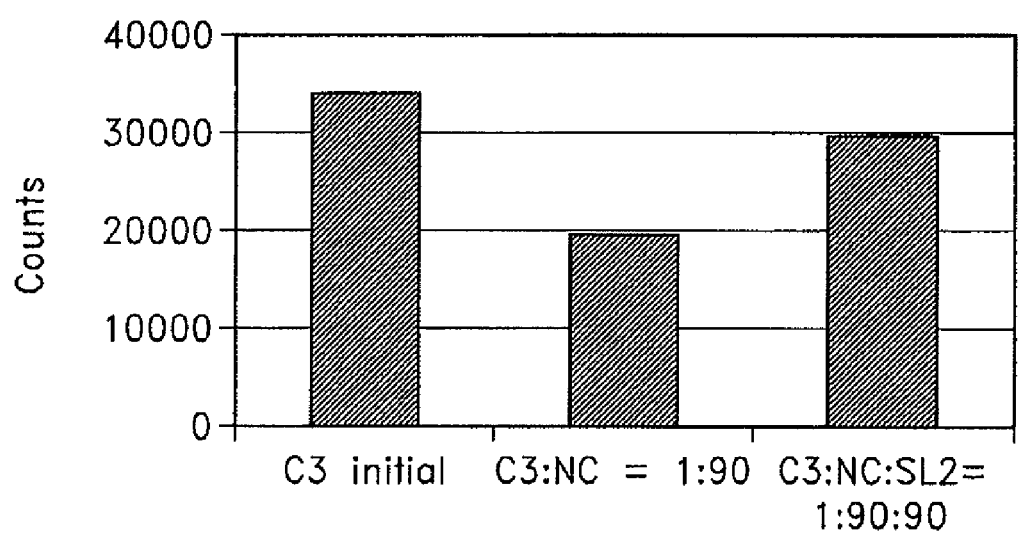
FIG. 9. Increase in fluorescence upon addition of SL2 to a quenched C3/NCp7 complex. [C3]≅10 nM.

FIG. 9 illustrates the results. The first bar shows the fluorescence intensity of the labeled C3 switch. The second bar shows the intensity after adding enough NC to switch a considerable fraction to the dark O-form. Addition of an amount of the SL2 inhibitor equal to the NC added produced a nearly instant response from C3 that is released from the P·O complex. The intensity increases again in the expected fashion. The degree of the increase is consistent with the equilibrium constants.

Figure 10:
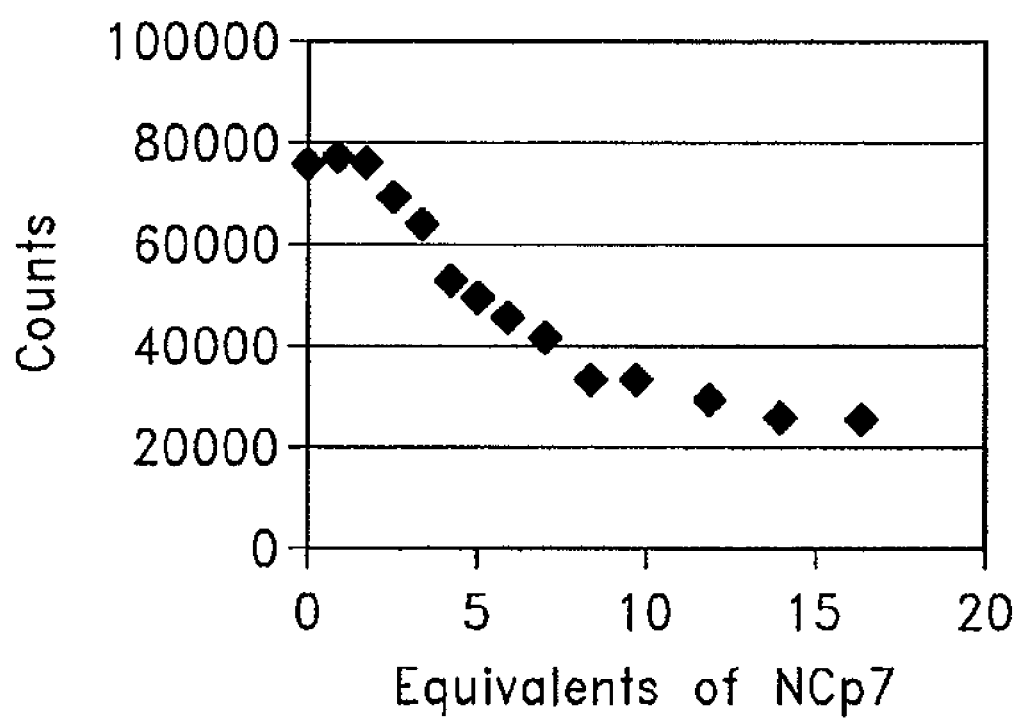
FIG. 10. Increase in fluorescence upon addition of SL2 to a quenched C3/NCp7 complex. [C3]≅10 nM.

Another experiment is illustrated in FIG. 10. Here, the competitor and NC-switch are premixed, and NC is added. SL2 and C3 were added to a cuvette and the C3 fluorescence was monitored as a function of [NCp7]. SL2, which has a higher affinity for NC, out-competes C3 for NC binding. This competition appears as an initial plateau in quenching (FIG. 10). This experiment also demonstrates that a high affinity NC competitor can interrupt formation of the switch-NC complex. The intensity decrease is again consistent with the equilibrium constants.

We also showed that the switch does not respond to the addition of bovine serum albumin at twice the concentration of NC used in these experiments. Neither does the switch respond to the addition of tap water, nor to water that contains human saliva (not shown).

Example 4

Luminescent Nucleic Acid Switches

Figure 11:
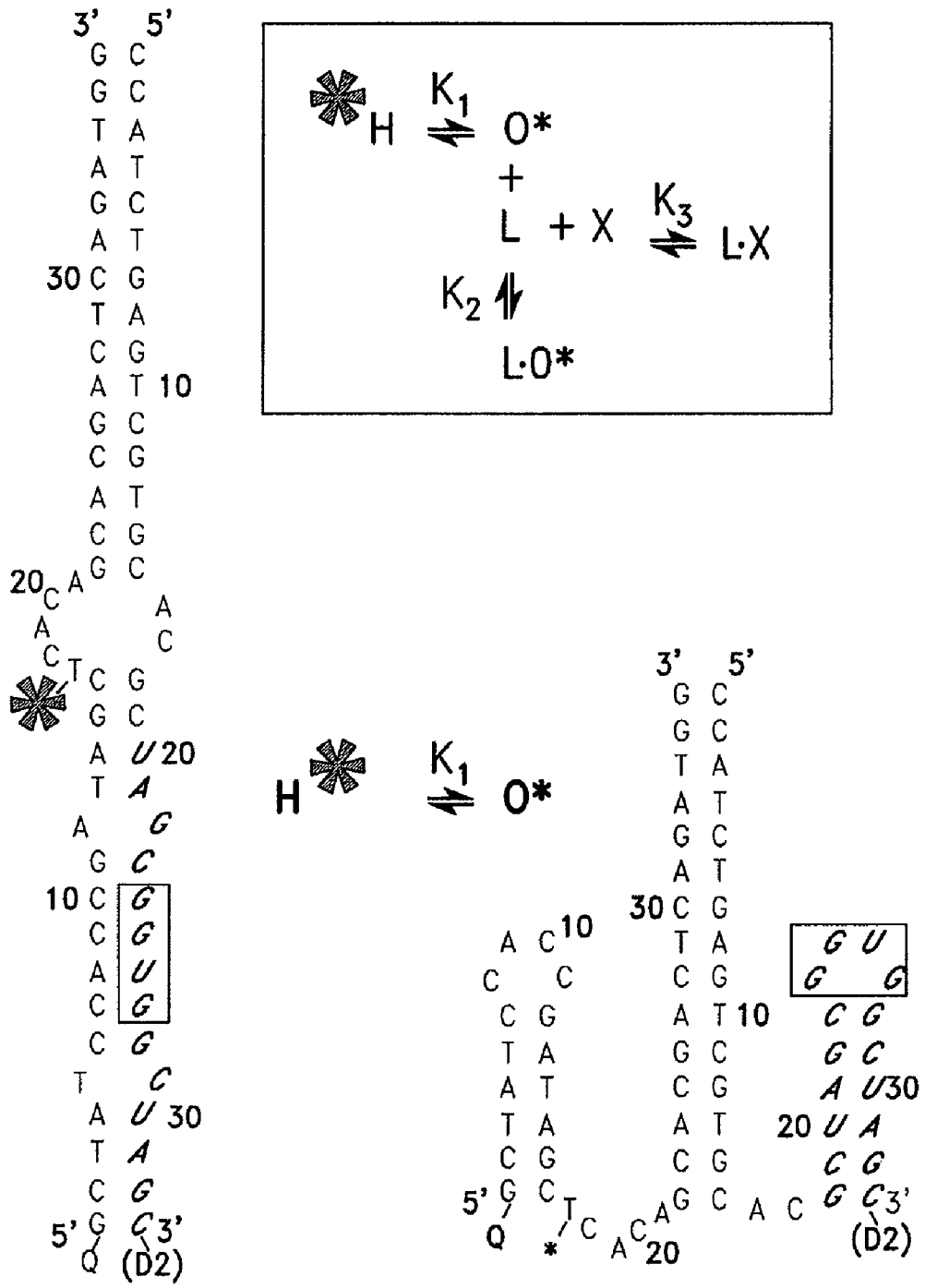
FIG. 11 shows the equilibria for the SL3-NCp7 assay using a tethered luminescent switch in accordance with the first embodiment of the present invention. The outline of a luminescence assay used to detect competitors of SL3-NCp7 complex formation is shown in the inset (top right). The sequences denote a tethered switch with two stable states: one where the binding site (GGUG sequence) is hidden, H, at left, and one where the binding site is open, O, at right. RNA segments are denoted in dark italics, DNA in lighter font. Tethering is accomplished by the fifteen base-pair stem that does not vary between the two states of the switch. The figure shows M3 (SEQ ID NO: 3) and D2 (SEQ ID NO: 6) as the two strands.

FIG. 11 shows the equilibria for the SL3-NCp7 assay using a tethered luminescent switch in accordance with the first embodiment of the present invention. The outline of a luminescence assay used to detect competitors of SL3-NCp7 complex formation is shown in the inset (top right). The sequences denote a tethered switch with two stable states: one where the binding site (GGUG sequence) is hidden, H, at left, and one where the binding site is open, O, at right. RNA segments are denoted in dark italics, DNA in lighter font. Tethering is accomplished by the fifteen base-pair stem that does not vary between the two states of the switch. This "fastener" stem is fixed, i.e., its sequence does not vary in optimizing the performance of the switch. The probe segment, P, is embodied in the RNA sequence, G18-C33, in the chimeric strand. The cover segment, C, is embodied in the sequence, G1-C16, of the all-DNA strand. L=Ligand, C=competitor, *=lumiphore, Q=quencher, D2=location for * if it is desired to make the signal of O-form highest and the H-form lowest. See [0055]-[0057] for definitions of equilibrium constants, $K_1$, $K_2$, and $K_3$.

The FRET system outlined in FIG. 11 can be configured to detect the presence or absence of NC-RNA complexes, and can be adapted to nearly any other protein-RNA or protein- DNA complex. For the SL3-NCp7 equilibrium, the SL3 RNA hairpin is available at the right of the RNA/DNA chimeric strand in the O-state. This switch has fluorescent labels, * (e.g., FAM, 6-carboxy-fluorescein), at position 17 of the all-DNA chain and Q (a quencher, e.g., dabcyl) at the 5'-end of the DNA segment (light font). Any luminescent label and quencher now known in the art may be used in the switches of the present invention. In the O species, * and Q are within the Förster distance for efficient quenching. However, they are far apart in the H-form, and the switch emits strongly.

By altering the DNA sequence, $K_1$ is adjusted between 0.1-0.01 ($K_1$=[O]/[H]). This gives 90-99% of the maximal luminescence signal in the absence of the other components. Upon addition of NCp7 (L), the $K_1$ equilibrium shifts to the right, and the luminescence signal decreases. The switch is set to a minimal signal in the presence of a slight excess of L, and is triggered to emit when a competitor, X, sequesters the protein in the L·X complex. The luminescent nucleic acid switches of the present invention share some properties with the "scorpion" probes used in real-time PCR applications (Solinas, A. et al. (2001) *Nucleic Acids Res* 29, E96; Thelwell, N. et al. (2000) *Nucleic Acids Res* 28:3752-61). Knowledge of $K_1$, $K_2$, and the input concentrations, $O_t$, $L_t$, and $X_t$ will allow estimation of $K_3$.

The bistable nature of the free switch and switch-protein complex is related to thermodynamic properties. The populations of the species will reach an equilibrium state that can be predicted with confidence from thermodynamic databases (Sugimoto, N. et al. (1995) Biochemistry 34:11211-6; SantaLucia, J. (1998) Proc Natl Acad Sci USA, 95, 1460-1465; Mathews, D. H.; Sabina, J.; Zuker, M.; Turner, D. H. (1999) J Mol Biol 288, 911-940; Zuker, M. (see web site: bioinfo.math.rpi.edu/~zukerm). The procedure is analogous to using two entries in the free energy tables in a physical chemistry text to predict the equilibrium constant for a third reaction. While such tables in chemistry texts are often accurate to 0.01 kcal/mol, the DNA/RNA databases have uncertainties on the order of 1 kcal/mol. That is enough to change the populations of the free and protein-bound switches by nearly an order of magnitude. However, as shown in Table 2, a few changes to the sequence can change K1 by twelve orders of magnitude. Therefore, one of skill in the art could readily fine-tune the equilibrium constant K1 by changing the sequence, and then monitoring the populations of the two species by measuring luminescence in accordance with the present teachings.

A multiwell, array or microarray format may be applied in accordance with one preferred embodiment of the present invention to screen small-molecule inhibitors for their potential to bind NCp7 or NC-containing precursors. It can be determined whether a compound permanently inactivates L or O, or releases the lumiphore by hydrolysis of the nucleotide chain. Titrations or bracketing tests can be used to classify "hits" in these screening assays. Hits will also be subjects for a "minus L" control; interference from competitor-nucleic acid interactions might be apparent from adding competitor to a luminescent switch with $K_1$=10-100. Changing the location of the quencher to the 3'-end of the RNA segment can also be used to make confirmatory tests. In that case, the O form is highly luminescent, and the assay will show a null for effective competitors.

Embodiments of the invention are directed to bistable A1/A2-constructs can be designed to detect competitors for other A2-L or A1-L complexes other than the HIV-1 nucleocapsid protein. Applications include RNA-protein interactions where the RNA binding site can be designed into the O-form. These include the RRE-rev and TAR-tat RNA-protein complexes in HIV-1. Other competitors of naturally occurring DNA-protein or RNA-protein complexes can be designed where the favored binding site for L occupies an analog of the O- or H-form. This design feature of the present disclosure distinguishes it from approaches based on combinatorially-derived sequences. However, the use of empirically chosen, rather than engineered, ligand binding domains is not precluded.

RNA or DNA molecules referred to as "aptamers" can be selected to bind nearly any protein or other molecular target (Jayasena, S. D. (1999) Clin. Chem. 45:1628-1650). An aptamer or other combinatorially-derived sequence binding site can be included in the A1- or A2-form, as well. The use of combinatorial technology to develop high affinity DNA- and RNA-protein binding sites represents an alternative to naturally occurring DNA- and RNA-protein binding sites described above. It is contemplated that high-throughput screens based on our invention can be developed for a wide array of therapeutic targets, remediation of bioterror agents, and other applications. It is also contemplated that sensitive and specific ligand-detection assays based on our invention could be developed for a wide array of proteins, nucleic acids, saccharides, toxins, and other molecules of diagnostic importance in humans, animals, plants, and other organisms, as well as for nearly instantaneous and specific assays for bioterror agents, and other applications.

Simple modifications to the scheme just described are required for the diagnostic applications. A competitor, X, does not need to be present for most diagnostic applications, in which case the K3 equilibrium in FIG. 11 is removed from consideration. The ligand-detection assay should give a minimal signal in the absence of L, and a strong signal when there is a substantial amount of the A2-L bound complex. One suitable alteration moves the luminescence donor, *, to the right-hand end of the chain shown in FIG. 11 (position D2). Then the H-form has a minimal signal because a lumiphore is near in space to a quencher. By contrast, the O-form is highly luminescent because the quencher is situated beyond the distance for efficient suppression of the signal. Other arrangements of lumiphore and quencher can be contemplated that would be useful to detect the state change.

Design Parameters for Luminescent Nucleic Acid Switches

The NC binding site. A basic design feature illustrated in FIG. 11 is to provide the highest affinity $G_2$-locus in the RNA loop with a stem identical to SL3; this feature is present at the right side of O in the figure. At the same time, the DNA and RNA hairpin loops are complementary to each other; GGUG will be double-stranded in H, and therefore unavailable to bind NC. The single-stranded DNA loop in O will not compete for NC, as we have shown that C-rich loops, and DNA loops in general, have much lower affinity (~10,000 times less for these d(CACC) loops). Note that we have chosen the GGUG loop sequence, which binds NCp7 more tightly than the wild-type GGAG (see Table 1; $K_2$ and $K_3$ are dissociation constants for the relevant complexes in this text).

Tuning the $K_1$ equilibrium. The switch design will preferably aim for 0.01<$K_1$<0.1 in the luminescence assays. A small $K_1$ value favors the "bright" H conformation, and will give a near maximal signal-to-noise ratio (S/N) when the system switches from the "dark" LO form. However, $K_1$ should not be too small or an extremely high affinity $K_2$ will be necessary to switch to LO. That is because the second equilibrium is concentration-dependent, and $O_t$ and $L_t$ will be ~0.1-10 μM. Preferred S/N will result if [H]/([O]+[LO])>3 at reasonable $L_t$ values in the presence of an interesting competitor. Thus, when $K_2$ is ~10-20 nM, $K_1$ is preferably set to trip the switch from off to on over a small increase in $X_t$.

The $K_1$ equilibrium is adjusted by changing the sequence of the all-DNA strand, particularly near positions 4, 8, or 13 (see FIG. 11). When these residues are all complementary to their RNA counterparts, H has four base pairs more than are present in the DNA and RNA stems of O. Then H will dominate the $K_1$ equilibrium. The stabilities, $\Delta G^{\circ}(H)$ and $\Delta G^{\circ}(O)$, can be estimated from thermodynamic databases (Sugimoto, N. et al. (1995) *Biochemistry* 34:11211-6) for forming a folded structure of DNA, RNA, or a DNA/RNA hybrid from the unstructured coils. The difference in free energy for the two forms is $\Delta G_1^{\circ} = \Delta G^{\circ}(O) - \Delta G^{\circ}(H)$ since their unstructured reference states are identical. We have estimated the free energy for 22 sequences and find that by forcing mismatches in H that are compensated in O, $K_1$ can be varied over 12 orders of magnitude. Several of these put $K_1$ in the preferred range for the applications disclosed herein. It is be within the ability of a person skilled in the biophysical chemistry of nucleic acds to construct an O⇔H system with the desired properties starting from the disclosed predictions.

Table 2 provides guidance to the skilled practitioner in calibrating the $K_1$ equilibrium. The bright state, H, has been characterized as the fully paired 40mer, M1, with * and Q as in FIG. 11b, and the properties of the dark state were demonstrated by the M2 molecule, which favors O by a factor of ~4000 over H. The latter has $K_2$ similar to that of SL3 RNA; this was tested using the Trp-assay. The luminescent switches, M2-M5, should be bright in the absence of NCp7 and dark in its presence (this has been verified for M2). Each of the molecules disclosed herein has been tested with MFOLD (see web site: bioinfo.math.rpi.edu/~zukerm) to ensure that no alternative secondary structure will be present. Note that the lengths of the base-paired stems, exact positions of the lumiphore and quencher, and detailed sequence can vary from that presented for M1 through M5, and still fall within the bistable H/O classification encompassed within this disclosure.

TABLE 2

Predicted K1 and mismatch sites for four molecules compared to the fully paired H chimera, M1*

| POSITION | M1 | M2 | M3 | M4 | M5 |
|---|---|---|---|---|---|
| 3 | T | A | | | |
| 4 | A | T | | T | |
| 5 | G | | T | | |
| 8 | A | T | | | |
| 9 | C | | | | AAA |
| 12 | C | | A | | |
| 13 | T | A | | A | |
| 14 | A | T | | | |
| $K_1$ | $6 \times 10^{-9}$ | $4 \times 10^3$ | 0.08 | 0.003 | 0.002 |

*Blank entries signify that the site has the same base as in M1; the full M1 sequence is given in FIG. 11.

The full sequences for the all-DNA chains in the M1-M5 tethered duplexes (SEQ ID Nos. 1-5, respectively) are:

```
                                        (SEQ ID NO: 1)
M1_DNA = dabcyl-d(GCTAGCCACCGCTAGC(T-FAM)-C
ACAGCACGACTCAGATGG);

(SEQ ID NO: 2)
M2_DNA = dabcyl-d(GCATGCCTCCGCATGC(T-FAM)-C
ACAGCACGACTCAGATGG);

(SEQ ID NO: 3)
M3_DNA = dabcyl-d(GCTATCCACCGATAGC(T-FAM)-C
ACAGCACGACTCAGATGG);

(SEQ ID NO: 4)
M4_DNA = dabcyl-d(GCTTGCCACCGCAAGC(T-FAM)CA
CAGCACGACTCAGATGG);

(SEQ ID NO: 5)
M5_DNA = dabcyl-d(GCTAGCCAAAACGCTAGC(T-FAM)-
CACAGCACGACTCAGATGG;
```

The DNA/RNA chimeric chain is constant in each of the tethered duplexes, M1-M5, having the full sequence;

```
                                        (SEQ ID NO: 6)
d(CCATCTGAGTCGTGCACGC)-UAGCGGUGGCUAGC;
```

The DNA residues are denoted by "d(XXX)" and RNA residues are not enclosed by parentheses; sequence alterations from M1 (also shown in FIG. 11) are underlined. The fluorophore (FAM=6-carboxymethylfluorescein) and universal quencher (dabcyl, methyl red) are well-known to practitioners skilled in FRET technology. The dabcyl label can be attached via a 5'-phosphate at the 5'-end of the DNA chain, T-FAM derives from the replacement of the 5-methyl of T by FAM; both dyes can be incorporated via ordinary solid-phase coupling or modification after solid-phase synthesis using standard methods.

In some embodiments the databases can predict only the order of magnitude of $K_1$. Therefore, experiments with two to four mismatched variants may be required to tune the assay for optimal switching performance. It is likely that the order of free energies predicted from the databases is correct, even if the actual values are not. For instance, if $K_1$ is found to be too small for best performance, an all-DNA strand predicted to favor O more strongly can be substituted.

Annealing strands tethered by duplexes. The strands of a switch that are tethered by a fastener duplex may be annealed to each other prior to conducting experiments related to the detection of ligand or a competitor binding. This can be conducted by standard methods familiar to one skilled in biophysical chemistry. A suggested process is to mix equimolar concentrations (near 1 micromolar) of strands at an ionic strength between 0.1-0.5 M, pH between 6-8. The strands can then be annealed by slowly reducing the temperature from 80° C. to room temperature over a period of 10-20 min.

Equimolar mixing of strands will be accompanied by maximum luminescence if the signaling arrangement described in FIG. 11 is used. A 5% molar excess of the DNA/RNA chimeric strand over the all-DNA strand in FIG. 11 will not affect most molecular switching applications, as ligand complexes with this chimeric strand will produce no signal and compete to an extent ≦5% with the tethered switches. A 5% molar excess of the all-DNA strand over the chimeric strand may result in a background luminescence signal that is higher than for a 1.00:1.00 mixture of strands. However, unannealed all-DNA strands will not form a high-affinity complex with the ligand, so these isolated strands will not compete effectively with the tethered switches.

Some applications may benefit from a tethering duplex, F, longer or shorter than the fifteen base pairs depicted in FIG. 11. In addition to estimating the free energy of duplex formation ($\Delta G^{\circ}_f$) using the standard thermodynamic databases, it is prudent to measure $\Delta G^{\circ}_f$ using the DNA strands that compose F. In the example posed by FIG. 11, the strands, d(AGCAC-GACTCAGATGG) and d(CCATCTGAGTCGTGCA) encompass F and "dangling" single-stranded A residues that contribute to stabilizing the duplex against strand dissociation. $\Delta G^{\circ}_f$ for F can be measured under the ionic strength and pH conditions contemplated for use of the switch. The equilibrium constant for duplex formation can then be calculated at the concentration of switch contemplated for use of the switch. Absorbance vs. temperature profiles, calorimetry, or other experimental techniques can be used to measure $\Delta G°_f$. This process is familiar to scientists skilled in the biophysical chemistry of nucleic acids.

One could have a concern that the hairpin-forming elements of the switches might dimerize. However, when the dimerization equilibrium constant is estimated from the thermodynamic databases, and the concentrations for the luminescence applications are used, the amount of such dimers is vanishingly small.

Simulating the binding equilibria. Optimizing performance of the assays and analyzing the results may be greatly assisted by simulations with input values of $K_1$, $K_2$, $K_3$, $O_t$, $L_t$, and $X_t$. The coupled equilibria describing all of the species result in a cubic equation for the luminescence competitor assay. This requires special treatment to solve for roots that are physically reasonable and that allow continuous variation of $X_t$ or other species in simulating titrations (Press, W. H. et al. *Numerical Recipes*, Cambridge U. Press, New York, 1986).

Figure 12:
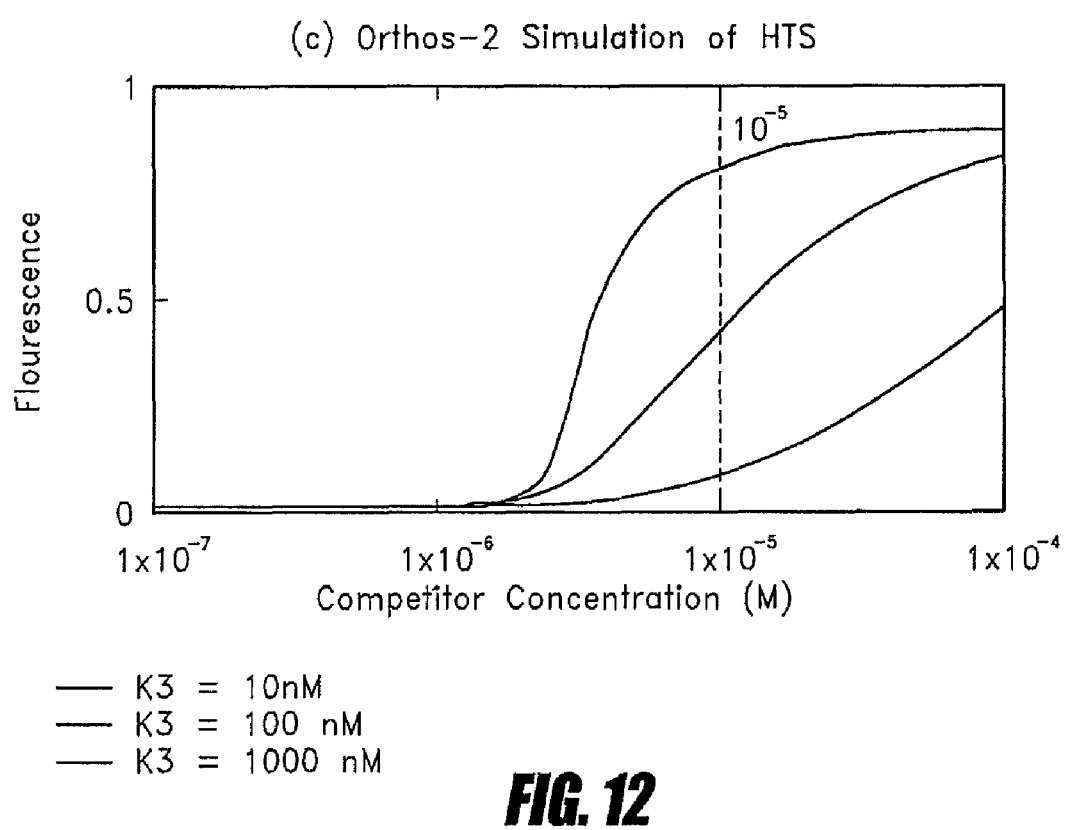
FIG. 12 shows competitor thresholds for the luminescent RNA/DNA chimera illustrated in FIG. 11, total concentration of switch molecules, $O_t$=0.3 µM, total concentration of ligand molecules, $L_t$=3 µM, $K_1$=0.1 nM, $K_2$=3 nM. Values of $K_3$ are indicated below the graph. See [0055]-[0057] for definitions of equilibrium constants, $K_1$, $K_2$, and $K_3$.

FIG. 12 illustrates the performance characteristics of a high throughput screening assay. At the dashed vertical line, $X_t$=10 μM, which is often used for testing libraries of chemical compounds. The simulations are helpful in adjusting the assay conditions for lower or higher-affinity competitors, other concentrations of competitors, etc.

Dynamic range is a function of the input variables $K_1$, $K_2$, $O_t$, $L_t$, and $X_t$. Under the conditions at the dashed line in FIG. 12, a dynamic range of 100 in $K_3$ can be distinguished in one well of a microtiter plate. Other wells can have other values for the input parameters. A dynamic range of 10,000 is reasonable for two or more wells per sample.

For low-affinity inhibitors, high concentrations are required and sensitivity is not an issue. Sensitivity is important for luminescence assays of the present invention only when the inhibitor affinity is so high that very low protein and inhibitor concentrations are needed to force appreciable dissociation of the complex. At that point, it is not necessary to measure an exact $K_d$—instead, one may need ADME/Tox assays to determine whether this is a bona fide drug lead.

Synthetic considerations. The luminescent chimeric switches tethered by fastener duplexes are made in two pieces. The "left-oligo" (left side of the H and O forms in FIG. 11) is composed exclusively of DNA and contains both the * and Q labels. The right-oligo contains both DNA and RNA and the D2 luminescence donor only for switches that are designed to give maximal luminescence upon binding the ligand. We have found that only the SL3 loop needs to be RNA for efficient NCp7 binding (last entry in Table 1). Increasing the number of DNA bases, especially at the ends of the chains (away from the ligand binding site), increases the stability of switches against contamination by ribonucleases. Current solid-phase synthesis technology can produce 30-50mer DNA, RNA, and chimeric strands in high yield. Signaling entities, such as FAM, dabcyl, etc., can either be added during solid-phase synthesis by incorporating the appropriately protected phosphoramidite, or by common procedures that add the labels after solid-phase synthesis is complete.

It is routine to purify 20mer-40mer length molecules by anion-exchange HPLC. Reversed-phase HPLC is also useful for purifying luminescently tagged oligomers from unlabeled versions. In some cases, especially with molecules that are >30mers, it is desirable to purify molecules by polyacrylamide gel electrophoresis (PAGE). Non-denaturing PAGE and Gel filtration chromatography are useful in purifying tethered duplexes from isolated single strands.

The extra flexibility in assembling the duplexes will prove valuable. The RNA side has only one sequence. It will be useful to have many sequences available for the all-DNA side to facilitate calibrating the $K_1$ switch at different levels. This is also useful in ranking competitors in several categories that differ in $K_3$.

Based on fluorescence quantum yields, the signal from the fluorescein analog, FAM, in the switches of the present invention are 20-50 times larger per photon absorbed than for our standard Trp-assay. A visible wavelength laser can be used to excite FAM, whereas a lower intensity UV lamp must be used for Trp. Detection also has a reduced background for visible compared to UV emission. Therefore, the signal/noise ratios for unquenched FAM will be 100-1000 times larger than for unquenched Trp. This sensitivity is comparable to $^{32}$P-labeling, without radiation concerns or the approximations that are required to interpret filter-binding assays.

It is appropriate to examine the two extreme states in FIG. 11 (sequences M1 and M2 in Table 2). This allows evaluation of the position of the $K_1$ equilibrium shift upon changing the sequence. Simply put, the luminescence of pure H and O are known, so their populations in a mixed system are just linear functions of the measured luminescence.

Improvements may be effected by using a construct that brings the * and Q labels closer together in the O-state, or introduces a fluorophore-quencher pair that more efficiently suppresses fluorescence at short distances (Integrated DNA Technologies, (www.idtdna.com); Coty, C. (2002) *Drug Discovery & Development* 5: 44-51; (www.nanoprobes.com). Even at a 2-fold difference in fluorescence between H and O, the sensitivity of the experiment is far higher than for the Trp-quenching assay. Another possible mode of the present invention is to use the difference in fluorescence lifetimes of the free and protein-bound switch. One expects the fluorophore to have a longer fluorescence lifetime when bound to NC than when it is free in solution. With phase modulation methods (modulated light intensity and a lock-in amplifier) one can get a steady state signal that attenuates the contribution from the short time component. There are commercial applications of phase modulation technology in high-throughput screening (Kashem, M. A. (2001) 5th Intl. Drug Disc. Prod. Users Mtg; (www.zymark.com); www.moleculardevices.com). The use of phase modulation in preferred embodiments of the present invention are expected to yield an increase in on/off discrimination of about 100-fold.

Other fluorophore quencher pairs which may be used in accordance with preferred embodiments of the present invention include those listed in the Integrated DNA Technologies catalog (www.idtdna.com/program/catalog/DNA_Probes_main.asp) and the Molecular Probes catalog (www.probes.com/servlets/masterlist). Of particular utility in construction of the switches disclosed herein are the following quenchers: dabcyl, BHQ-1, BHQ-2, Iowa Black, and Nanogold, and the fluorophores, 6-FAM, TET, HEX, Cy3, Cy5, eosin, coumarin, Oregon Green, Rhodamine Green, Rhodamine Red, Texas Red, TAMRA, ROX, JOE, Bodipy dyes. Of course any other quenchers known in the art are also considered applicable to construction of the fluorophore quencher pairs disclosed herein.

Others have proposed bimolecular RNA-RNA or DNA-DNA probes that could produce similar results to the switches disclosed herein for high-throughput screens (Jayasena, S. D. (1999) *Clin. Chem.* 45:1628-1650). However, these applications have been designed such that the screen has probes switch between single-stranded and duplexed states. This brings the unavoidable fact that the kinetics of forming the complex are second-order, and thus concentration dependent. For example, we experimented with a bimolecular complexation system (i.e., removing the fastener duplex tether in FIG. 11). At the low concentrations typically used in fluorescence assays, the time for nearly complete equilibration was ~10 hr at room temperature. While a high-throughput assay for competitors is still possible, it would require either a long equilibration time, or annealing by heating. It would be preferable to avoid heating in the presence of a ligand or competitor that might denature. Using untethered bimolecular probes it may be awkward to perform titrations for determining accurate $K_3$ values. Simulations may also be more difficult, involving equations that are fifth-order in some of the variables. This may make designing the assays more difficult, as well as complicating interpretation of the results.

There is another aspect of kinetics that may be significant in regard to certain aspects of the present invention. For example, with respect to the bistable tethered switches of the present invention, the system must go through a partially paired intermediate to convert from one state to the other. There will be an associated activation barrier that slows the conversion between the two forms. The barrier probably depends on the length of the stems in the hairpins segments. Therefore, we prepared a 16mer SL3 construct, which has two base pairs removed from the 20mer SL3 stem used previously. The Trp-assay showed that both have virtually identical $K_d$ values. The 16mer has been incorporated in a preferred embodiment of the luminescent switch design (FIG. 11), and we have shown that equilibration with NCp7 has been shown to occur within a minute at a 10 nM concentration of the M3 switch. Another aspect favoring rapid equilibration across $K_1$ is the chaperoning aspect of NCp7, which allows even lambda DNA to quickly adjust to its lowest free energy form under force-induced stretching.

Competitor Binding

The experiments outlined below start with applications of known competitors of the NC-RNA complex then move to those that have the potential to become useful drugs directed against new anti-HIV targets.

Ligands with known affinity. The Trp-assay cannot determine the affinities very well for tight-binding ligands of NCp7. Reviewing FIG. 5 reminds us that titrations for such ligands will deviate only slightly from the dashed 1:1 line for $K_d$=0. The deviation is largest when the complex approaches saturation, so only a few data points control the value determined for $K_d$. Since the deviation and the S/N are small for these points, the effect of experimental errors is large.

The luminescence-quenching assays using the switches of the present invention offer a method to determine $K_d$=$K_3$ by competition, such as with SL3-GGUG. As shown in FIG. 12, the assay is capable of determining $K_3$ accurately. The assay effectively balances $K_3$ against $K_2$ and $K_1$, so a titration provides many high S/N data points. Switch molecules can be tested by determining whether they reproduce known $K_d$ values. For instance, NC-switches can be tested with the RNA molecules listed in Table 1. Good choices would be SL2, SL1a and SL4, which have no appreciable complementarity to any part of the switch.

Measurements of unknown affinities RNA aptamer constructs selected against NCp7 for which nanomolar affinities have been asserted from measurements at low salt concentrations (Lochrie, M. A. et al. (1997) *Nucleic Acids Res* 25:2902-10; Berglund, J. A. et al. (1997) *Nucleic Acids Res* 25:1042-9; Allen, P. et al. (1996) *Virology* 225:306-15), have been studied with our tryptophan assay. The aptamer construct sequences have been published, and appropriate RNA molecules are available commercially, which were purified by standard methods. Some of these aptamer constructs do not have obvious $G_2$-loci, and could be very useful in expanding our general understanding of the basis for NC-RNA binding specificity. However, we have shown that these published aptamer constructs bind two or more NCp7 proteins per RNA, rendering them marginally useful in drug discovery applications. Other RNA constructs we have inferred from aptamer sequences have 1:1 stoichiometry and affinity for NCp7 that is similar to SL3 and SL2.

The cyclic peptide, c(F-C-dW-R-C-K), has been shown to have effects that suggest it competes with NCp7 (Druillennec, S. et al. (1999) *Proc Natl Acad Sci USA* 96:4886-91). This luminescence-quenching assay would not be done in the competition mode described above. Instead, the quencher should be located at the D2 position in FIG. 11, and the dominant H-species will be dark. If the peptide binds to O, the switch will light and allow measurement of $K_d$=$K_2$. If the c(F-C-dW-R-C-K) competition is favorable, other cyclic peptides may be used in accordance with this embodiment of the present invention.

The competitor binding tests allow us to measure affinities of compound libraries in a high-throughput fashion. They also provide a means to determine whether designed or combinatorial changes improve the affinity of anti-NC candidates.

Other Target Interactions

In addition to the interactions between the viral RNA and the NC domain described above, any other target interactions with RNA, DNA, proteins, precursors, and saccharides may be exploited in accordance with the present disclosure. Some of these targets include, without limitation, the internal ribosome entry site (IRES) of Hepatitis C Virus, IRES sites in other viruses, as well as agents involved in the etiology of viral infections related to Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, and targets in HIV-1, MMTV, HIV-2, HTLV-1, SNV, BIV, BLV, EIAV, FIV, MMPV, Mo-MLV, Mo-MSV, M-PMV, RSV, SIV, AMV, and other related retroviruses, including but not limited to: TAR-tat, RRE-rev, DIS, PBS, RT, PR, IN, SU, TM, vpu, vif, vpr, nef, mos, tax, rex, sag, v-src, v-myc and precursors and protease products of the precursors: gag, gag-pol, env, src, one, as collected in Appendix 2 of Coffin, J. M., Hughes, S. H., Varmus, H. E. (1997) Retroviruses, Cold Spring Harbor Lab Press, Plainview, N.Y.). Other targets in bacteria, fungi, insects, and other pathogens and pests of humans, animals, and plants may also be applicable to the present switches and methods, including but not limited to *B. anthracis*, (especially the components of the toxin: protective antigen, lethal factor, edema factor, and their precursors), *Burkholderia pseudomallei, Botulinum toxins, Brucellosis, Candida albicans, Cholera, Clostridium perfringins toxins, Kinetoplasts, Malaria, Mycobacteria, Plague, Pneumocystis, Schistosomal parasites, Cryptosporidium, Giardia*, and other environmental contaminants of public and private water supplies, Ricin, Saxitoxin, Shiga Toxin from certain strains of *E. coli*, *Staphylococcus* (including enterotoxin B), Trichothecene mycotoxins, Tularemia, and agents causing Toxoplasmosis, as well as contaminants of food and beverages that may be deleterious to human or animal health. The detection and screening methodologies afforded by some embodiments of this invention may also be applied to small-molecule targets, including but not limited to nerve gas agents and chemical poisons, as well as contaminants of public and private water supplies, of food and beverages, and of indoor air that may be deleterious to human or animal health.

Example 5

Branched Nucleic Acid Switch

Embodiments of the invention are directed to an RNA/DNA chimeric switch with three branches which include a "probe" segment, P, a "cover" segment, C, and a "toggle" segment, T. P contains one or more high affinity sequences for a target molecule, C is completely or nearly complementary to P, and T is mostly complementary to P, such that a large population of the switch molecules include C:P stems and a smaller population includes T:C stems. An appropriate combination of signaling entities is attached to the strand termini to conveniently read out the relative populations of the stable states. It is also contemplated that multiple switches embodying different probe strands could have coordinated activities. Applications of the latter may include sensing cascades that amplify the response of a first switch. This could lead to multi-unit molecular amplifiers, state-switchable nanostructures, and/or multi-unit molecular nanomachines.

The three-fold connection in FIG. 8 can be made using a "doubler" phosphoramidite originated for the creation of nucleic acid dendrimers (http://www.glenres.com/ProductFiles/Technical/TB_dC_Brancher.pdf; T. Horn and M. S. Urdea, *Nucleic Acids Res,* 1989, 17, 6959-67; M. L. Collins, et al., *Nucleic Acids Res,* 1997, 25, 2979-84; T. Horn, C. A. Chang, and M. S. Urdea, *Nucleic Acids Res,* 1997, 25, 4842-4849; T. Horn, C. A. Chang, and M. S. Urdea, *Nucleic Acids Res,* 1997, 25, 4835-4841). The central branch can also mimic the branched intermediate in RNA splicing, where the 2', 3', and 5'-OH groups of an RNA nucleotide all bear phosphodiesters connecting to each of the three chains.

FIG. 13 illustrates the embodiment in which P, C, and T are fastened at a single vertex, thus comprising a unimolecular switch. FIG. 13(*a*) shows a 3-fold junction connecting the P, C, T segments. The designation T_C_P denotes the unpaired random-coil reference state for free energy comparisons. The bistable molecule can exist in either the T_C:P state or the T:C_P state (FIG. 13(*b*)). The ligand binding site in P is sequestered in T_C:P and available in T:C_P. The population of TC:P is highest in the absence of ligand binding. The distances between the signaling entities, S, S', and S", change when the switch changes state.

A free energy diagram depicts relative and barriers to interconversion of states (FIG. 13(*c*)). In the absence of binding to the ligand, X, the low free energy form has P sequestered in the C:P complex. When T:C_P is not bound to X the switch has a higher free energy. The free energy of the T:C_P:X complex decreases as the concentration [X] increases, tipping the populations in favor of the T:C_P form of the switch. Interconversion between the two forms is slow if the intermediate form is similar to T_C_P, where most or all of the base pairs are broken. The two forms convert rapidly if the intermediate steps occur via branch migration, where only a few base pairs are broken in a helix defect that migrates from one end of the C segment to the other.

The sequences of the three segments can be engineered to create an efficient molecular switch (FIG. 13(*d*)). A "1" denotes a nucleotide complementary to a "2", and "3" is complementary to "4". The "combimer" contains the ligand binding site, in P, which is written 5'-3', left to right. The cover segment, C, written 3'-5', can be slightly longer than P, but otherwise is depicted as fully complementary. The toggle segment, T, is depicted as having a mismatch with C in the combimer zone, but is otherwise fully complementary. Several trials can be made to evaluate the effect of different base pairs and mismatches using the thermodynamic databases. This is necessary to ensure optimal performance of the switch by setting K1 at around 0.01 to 0.1 as in FIG. 11.

Analogs of Branched Nucleic Acid Switches Using a Tethering Duplex

Figure 14C:
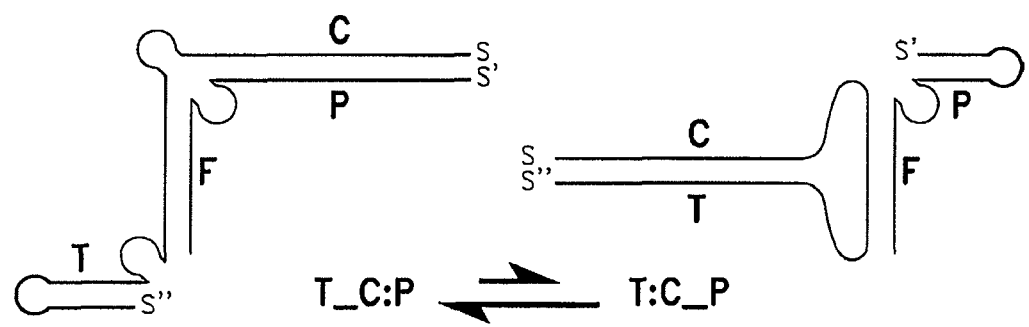

FIG. 14 illustrates three embodiments which are analogous to FIG. 13*b*. As in the embodiment illustrated in FIG. 11, the fastener stem, F, is stable and does not substantially alter during switching events. P, C, and T have the same meaning as in FIG. 13. Locations of signaling moieties, S, S', and S" can be optimized to create the most robust signal output. FIG. 14*c* resembles the secondary structure in a single chain of covalently attached residues formally known as a "pseudoknot."

FIG. 15 illustrates an embodiment in which P and C lie on separate strands, which are held together by stable fastener stems, F1 and F2. The construct in FIG. 11 has a similar appearance, with F2 being zero-length. The designation C_P denotes the open conformation where the probe segment is available to bind the ligand. The ligand binding site in P is sequestered in the C:P state. The folded form at the right is formally known as a cruciform structure. The distal ends of F1 and F2 may be joined, in which case P and C reside in a covalently closed circle that may be supercoiled. The density of supercoils can influence the C:P⇌C_P equilibrium.

Supercoiling in DNA is well-known (Cantor, C. R. & Schimmel, P. R. (1990) Biophysical Chemistry Part III, 1265-1290). It is easy to control the density of superhelical turns using intercalating dyes and topoisomerase enzymes (Wang, J. C. (1996) Annu. Rev. Biochem. 65:635-92; Wang, J. C. (1984) J. Cell Sci Suppl. 1:21-29). The helical nature of double-stranded DNA engenders a substantial resistance to supercoiling; this resistance can be tapped to switch the state of a localized domain to reduce the superhelical stress. The resistance can be quantified by a free energy, $\Delta G°(sup)$, which expresses the ability to cause chemical change upon relaxing the superhelical turns.

For example, the ends of the molecule in FIG. 15 could be joined to a long DNA double helix. The ends of these long DNA segments could be covalently joined to make an interwound pair of circles with the DNA side of the switch region on one strand, and the RNA side on the other. If the circular DNAs are twisted in the proper superhelical direction, enough energy can be stored to cause a local cross-shaped, "cruciform" that extrudes the P and C loops as in the right side of FIG. 15. This comes at a cost in free energy, $\Delta G°(cru)$. That is because base pairs are lost for the two loops at the ends of P and C, and there is additional disruption at the branch of the cross. When $\Delta G°(sup)$ has a large enough magnitude, the $\Delta G°(cru)$ penalty is overcome, and the cruciform extrudes. The point at which cruciform structures and double helix have equal populations in equilibrium is when $\Delta G°(cru)=\Delta G°(sup)$.

This sets up a very similar situation to that described above, where the K1 equilibrium constant was adjusted by changing the nucleic acid sequence to set the trigger for a large change in luminescence (O→H) to occur upon addition of a small amount of an effective competitor, C. If a ligand, like NCp7, is present in high enough concentration with the superhelical switch, it will bind the GGUG tetraloop and force the cruciform to occur at a lower density of superhelical turns. This can be quantified using free energies, which are additive; now the equal balance between cruciform and double-helical structures occurs when $\Delta G°(cru)=\Delta G°(sup)+\Delta G(L/P)$. The balance between the two sides of this equation can be adjusted so that addition of a small amount of competitor ties up enough L to reduce the ΔG(L/P) contribution, and switch the state away from the cruciform state. The adjustment in this case is accomplished by changing ΔG°(sup), which is a simple function of the number of superhelical turns. Sequence-based tuning, as illustrated earlier, combined with balancing via superhelix density is attractive for the development of suitable bistable constructs. Current procedures for creating superhelices create a range of superhelix densities and relaxed molecules; it may prove necessary to purify constructs within a relatively small range of superhelix densities.

Readout of the state of the cruciform/helix switch can again be accomplished by fluorophore-quencher pairs. If these are positioned near the cruciform loops, the cruciform state will be highly luminescent and the helix form dark. Positioning * and Q near the ends of the cover hairpin (analogous to FIG. 11) will produce the opposite result.

Molecular Electronic Applications

Certain molecular electronic applications can be realized using an embodiment of the present invention. This application also serves to illustrate methodology for integrating combinatorial sequence technology with H to O switching. For example, FIG. 16 outlines the heart of a Read/Write/Erase device for information storage. The top panel indicates that the oligonucleotide-lumiphore/quencher "switch" can exist in a "zero" or a "one" conformation that can be toggled by light of frequencies, v1 and v2. The state of the switch can be interrogated by light at v3; the zero state has a very low luminescence emission at v4, while the one state has robust emission. The device has only Read/Write capability if the zero to one conversion is not capable of being reversed by v2. (The energy of a photon is represented by hvi, where Planck's constant is h. The wavelength of light is $\lambda i = c/\lambda i$, where c=speed of light.)

The bottom panel of FIG. 16 illustrates an embodiment of the principles just discussed. An H-type molecule, similar to that in FIG. 11, is shown attached at its bottom to a solid support (S) via covalent attachment of one of the two strands of the fastener duplex; such a solid-support attachment may also be useful in some applications of the technologies described for diagnostics and screening presented previously. In molecular electronic applications this attachment provides spatial addressability. The embodiment illustrated in FIG. 16 has a very similar arrangement of lumiphore (*) and quencher (Q) to that illustrated in FIG. 11, and it can be seen that H to O conformational equilibria are still common features. However, a difference lies in the attachment of a photosensitive chemical entity to the 3'-end of the RNA/DNA chain by a flexible linker. The photochemical entity is illustrated in the figure as having two states, L1 which is converted to L2 by irradiation at v1; if the erase function is to be implemented, L2 must be capable of efficient back conversion by the action of v2. When the photochemical entity is in the L2 state, the O2 to H2 equilibrium will favor H2, just as in the screening interaction illustrated previously, and intense luminescence will occur due to the long distance between * and Q. Only the O-form of the construct has a binding pocket with high affinity for L1, but low affinity for L2. Thus, prior to irradiation at v1, the binding free energy of L1 for the binding pocket drives the equilibrium to favor the "dark" O1-form with very low luminescence emission. Although there are four states illustrated in FIG. 16, the concentrations of the H1 and O2 states will usually be very small; they are essentially intermediates in the pathway to converting between the stable O1 and H2 forms. The binding pockets for L1 and L2 can be optimized in combinatorial experiments with a large variety of sequences.

Molecules known as fulgides and fulgimides can exist in states where a central ring is open or closed photochemically. The forms can be cycled many times by the action of light at two different wavelengths (Wolak, M. A. et al. (2002) J. Photochem. Photobiol. A, 147:39-44). Many other photochemical entities have been characterized, as well (Willner, I. (1997) Acc. Chem. Res., 30:347-356). An o-nitrobenzyl photochemistry (Zhang, K. & Taylor, J.-S. (2001) Biochemistry, 40:153-159) is particularly useful for Read/Write (no erase) devices. Here the action of light at $\lambda 1 = 365$ nm cleaves the L1 ligand from the 3'-end of a DNA molecule. After cleavage, the effective concentration of L1 near the binding pocket is reduced by a large fraction, rendering the switch in the permanently "on" H-form.

Such devices are quite practical for sensitive Read/Write information storage applications. The domain size for luminescence detection and writing using laser light sources is limited only by diffraction at the wavelength used. Usually many fewer photons will be required for reading (luminescence) than for writing or erasing (photochemical rearrangement of bonds). Therefore, it is unlikely that reading will cause a sufficient amount of photochemistry to practically reverse the writing and erasing steps. A single addressable domain may contain molecules with different photochemical ligands, L1/L2. This can be used to provide wavelength discrimination within a domain in a manner similar to current plans for holographic data storage devices (Wise, K. J. (2002) Trends Biotechnol. 20:387-394). Likewise, different lumiphores with distinct absorption and emission spectra can provide multicolored detection.

Variations of Molecular Switch Morphology

Other arrangements of lumiphore, quencher, binding pocket, and molecular conformation are possible for switching devices within the scope of the present invention. It is also not a general requirement that the nucleic acid portion be chimeric for many applications involving combinatorially-derived sequence binding pockets.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method of chemical screening comprising:
providing a bistable branched switch, comprising DNA, RNA, modified nucleic acid, or combinations thereof, wherein the branched switch is adapted to switch from a first conformation to a second conformation upon ligand binding, said switch comprising:
  a probe strand P comprising a ligand binding domain;
  a switching framework comprising a cover strand (C), which is partially but not completely complementary to P;
  a tether that holds P and C together while the switch changes between the first and second conformations without dissociating the branched nucleic acid thereby creating a rapidly reversible switch;
  a toggle strand (T) tethered to the P-strand and the C-strand by covalent linkage; and
  a signaling apparatus comprising a combination of signaling entities, wherein a ligand for the ligand binding domain is selected from the group consisting of proteins, cell-surface features, and small molecules, and wherein the ligand binding domain is sequestered in the first conformation;
contacting the branched switch with the ligand in the absence of a screened chemical entity;
monitoring a signal produced from the signaling apparatus in the absence of the chemical entity;
contacting the branched switch with the ligand in the presence of the chemical entity;
monitoring a signal produced from the signaling apparatus in the presence of the chemical entity; and
comparing the signal produced in the absence of the chemical entity with the signal produced in the presence of the chemical entity to determine the effect of the chemical entity on the ligand binding.

2. The method of claim 1, wherein the signaling apparatus comprises a lumiphore and a quencher of the lumiphore.

3. The method of claim 1, wherein the ligand binding domain comprises RNA, the switching framework comprises DNA and the ligand is a viral protein.

4. The method of claim 1, wherein the ligand binding domain comprises RNA, the switching framework comprises DNA and the ligand binding domain comprises a naturally occurring RNA binding site or analog thereof or a naturally occurring DNA binding site or analog thereof or a combinatorially derived sequence or related fragment.

5. The method of claim 1, wherein the ligand binding domain comprises RNA, the switching framework comprises DNA and the ligand is selected from the group consisting of:
  a disease agent wherein the disease is Hepatitis C, Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, HIV-1, MMTV, HIV-2, HTLV-1, SNV, BIV, BLV, EIAV, FIV, MMPV, Mo-MLV, Mo-MSV, M-PMV, RSV, SIV, or AMV;
  a retroviral component which is TAR-tat, RRE-rev, DIS, PBS, RT, PR, IN, SU, TM, vpu, vif, vpr, nef, mos, tax, rex, sag, v-src, v-myc and precursors and protease products of the precursors, gag, gag-pol, env, src, or onc;
  a toxin or other factor derived from bacteria or other microorganisms which are *B. anthracis, Burkholderia pseudomallei, Botulinum, Brucellosis, Candida albicans, Cholera, Clostridium perfringins, Kinetoplasts, Malaria, Mycobacteria, Plague, Pneumocystis, Schistosomal parasites, Cryptosporidium, Giardia, Ricin, Saxitoxin, Shiga Toxin, Staphylococcus* (including enterotoxin B), Trichothecene mycotoxins, Tularemia, or agents causing Toxoplasmosis; and
  nerve gas agents, chemical poisons, contaminants of water supplies, contaminants of food and beverages, or contaminants of air.

6. The method of claim 1, further comprising equilibrating the molecular switch and the ligand prior to adding the chemical entity.

7. The method of claim 1, wherein P, C and T are joined together at a vertex.

8. A method of chemical screening comprising:
providing a bistable multichain switch, comprising DNA, RNA, modified nucleic acid, or combinations thereof, wherein the switch comprises a ligand binding domain and a signaling apparatus and, wherein the multichain switch is adapted to switch from a first conformation to a second conformation upon ligand binding, and wherein said switch comprises:
  a first strand comprising the ligand binding domain;
  a second strand; and
  a fastener to couple the two strands together without dissociating the multichain switch, thereby creating a rapidly reversible switch;
wherein the first strand and second strand hybridize to each other in the first conformation which sequesters the ligand binding domain and the ligand binding domain is free in the second conformation, wherein a ligand for the ligand binding domain is selected from the group consisting of proteins, cell-surface features, and small molecules;
contacting the multichain switch with the ligand in the absence of a screened chemical entity;
monitoring a signal produced from the signaling apparatus in the absence of the chemical entity;
contacting the multichain switch with the ligand in the presence of the chemical entity;
monitoring a signal produced from the signaling apparatus in the presence of the chemical entity; and
comparing the signal produced in the absence of the chemical entity with the signal produced in the presence of the chemical entity to determine the effect of the chemical entity on the ligand binding.

9. A method of chemical screening comprising:
providing a bistable multichain switch, comprising DNA, RNA, modified nucleic acid, or combinations thereof, wherein the multichain switch is adapted to switch from a first conformation to a second conformation upon ligand binding, said switch comprising:
  a probe strand P comprising a ligand binding domain;
  a switching framework comprising a cover strand (C), which is partially but not completely complementary to P;
  a tether that holds P and C together while the switch changes between the first and second conformations without dissociating the multichain nucleic acid thereby creating a rapidly reversible switch; and
  a signaling apparatus comprising a combination of signaling entities, wherein a ligand for the ligand binding domain is selected from the group consisting of proteins, cell-surface features, and small molecules, and wherein the ligand binding domain is sequestered in the first conformation,
wherein tethering occurs via a fastener duplex, F, to couple two covalently linked nucleic acid strands together by a non-covalent interaction, wherein the first strand comprises C and the second strand comprises P when the multichain switch is in the second conformation;

contacting the multichain switch with the ligand in the absence of a screened chemical entity;

monitoring a signal produced from the signaling apparatus in the absence of the chemical entity;

contacting the multichain switch with the ligand in the presence of the chemical entity;

monitoring a signal produced from the signaling apparatus in the presence of the chemical entity; and comparing the signal produced in the absence of the chemical entity with the signal produced in the presence of the chemical entity to determine the effect of the chemical entity on the ligand binding.

10. The method of claim 9, wherein the fastener duplex is a base-paired stem that does not vary between the first and second conformations of said switch.

11. The method of claim 8, wherein the signaling apparatus comprises a lumiphore and a quencher of the lumiphore.

12. The method of claim 8, wherein the ligand binding domain comprises RNA, and the ligand is a viral protein.

13. The method of claim 8, wherein the ligand binding domain comprises RNA, and the ligand binding domain comprises a naturally occurring RNA binding site or analog thereof or a naturally occurring DNA binding site or analog thereof or a combinatorially derived sequence or related fragment.

14. The method of claim 8, wherein the ligand binding domain comprises RNA, and the ligand is selected from the group consisting of:
   a disease agent wherein the disease is Hepatitis C, Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, HIV-1, MMTV, HIV-2, HTLV-1, SNV, BIV, BLV, EIAV, FIV, MMPV, Mo-MLV, Mo-MSV, M-PMV, RSV, SIV, or AMV;

a retroviral component which is TAR-tat, RRE-rev, DIS, PBS, RT, PR, IN, SU, TM, vpu, vif, vpr, nef, mos, tax, rex, sag, v-src, v-myc and precursors and protease products of the precursors, gag, gag-pol, env, src, or onc;

a toxin or other factor derived from bacteria or other microorganisms which are *B. anthracis, Burkholderia pseudomallei, Botulinum, Brucellosis, Candida albicans, Cholera, Clostridium perfringins, Kinetoplasts, Malaria, Mycobacteria, Plague, Pneumocystis, Schistosomal parasites, Cryptosporidium, Giardia, Ricin, Saxitoxin, Shiga Toxin, Staphylococcus* (including enterotoxin B), Trichothecene mycotoxins, Tularemia, or agents causing Toxoplasmosis; and nerve gas agents, chemical poisons, contaminants of water supplies, contaminants of food and beverages, or contaminants of air.

15. The method of claim 8, further comprising equilibrating the molecular switch and the ligand prior to adding the chemical entity.

16. The method of claim 9, wherein the signaling apparatus comprises a lumiphore and a quencher of the lumiphore.

17. The method of claim 9, wherein the ligand binding domain comprises RNA, the switching framework comprises DNA and the ligand is a viral protein.

18. The method of claim 9, wherein the ligand binding domain comprises RNA, the switching framework comprises DNA and the ligand binding domain comprises a naturally occurring RNA binding site or analog thereof or a naturally occurring DNA binding site or analog thereof or a combinatorially derived sequence or related fragment.

19. The method of claim 9, wherein the ligand binding domain comprises RNA, the switching framework comprises DNA and the ligand is selected from the group consisting of:

a disease agent wherein the disease is Hepatitis C, Congo-Crimean hemorrhagic fever, Ebola hemorrhagic fever, Herpes, human cytomegalovirus, human pappiloma virus, influenza, Marburg, Q fever, Rift valley fever, Smallpox, Venezuelan equine encephalitis, HIV-1, MMTV, HIV-2, HTLV-1, SNV, BIV, BLV, EIAV, FIV, MMPV, Mo-MLV, Mo-MSV, M-PMV, RSV, SIV, or AMV;

a retroviral component which is TAR-tat, RRE-rev, DIS, PBS, RT, PR, IN, SU, TM, vpu, vif, vpr, nef, mos, tax, rex, sag, v-src, v-myc and precursors and protease products of the precursors, gag, gag-pol, env, src, or onc;

a toxin or other factor derived from bacteria or other microorganisms which are *B. anthracis, Burkholderia pseudomallei, Botulinum, Brucellosis, Candida albicans, Cholera, Clostridium perfringins, Kinetoplasts, Malaria, Mycobacteria, Plague, Pneumocystis, Schistosomal parasites, Cryptosporidium, Giardia, Ricin, Saxitoxin, Shiga Toxin, Staphylococcus* (including enterotoxin B), Trichothecene mycotoxins, Tularemia, or agents causing Toxoplasmosis; and nerve gas agents, chemical poisons, contaminants of water supplies, contaminants of food and beverages, or contaminants of air.

20. The method of claim 9, further comprising equilibrating the molecular switch and the ligand prior to adding the chemical entity.

* * * * *

UNITED STATES PATENT AND TRADEMARK OFFICE
CERTIFICATE OF CORRECTION

| | |
|---|---|
| PATENT NO. | : 8,080,379 B2 |
| APPLICATION NO. | : 12/901762 |
| DATED | : December 20, 2011 |
| INVENTOR(S) | : Borer et al. |

It is certified that error appears in the above-identified patent and that said Letters Patent is hereby corrected as shown below:

Column 1, Line 66, "*Rev. Med. Viral.*" should be changed to --*Rev. Med. Virol.*--

Column 3, Line 23, "human pappiloma virus," should be changed to --human papilloma virus,--

Column 3, Line 32, "or one;" should be changed to --or onc;--

Column 3, Line 36, "*Clostridium perfringins*," should be changed to --*Clostridium perfringens*,--

Column 4, Line 52, "human pappiloma" should be changed to --human papilloma--

Column 4, Line 61, "or one;" should be changed to --or onc;--

Column 4, Line 65, "*Clostridium perfringins*," should be changed to --*Clostridium perfringens*,--

Column 7, Line 31, "resonance energy transfer," should be changed to --resonance energy transfer.--

Column 9, Line 63, "Oertle S, and" should be changed to --Oertle S. and--

Column 11, Line 30, "*Proc Nall Acad Sci USA.*" should be changed to --*Proc Natl Acad Sci USA.*--

Column 15, Line 7, "($1K_d$; similar to" should be changed to --$1/K_d$; similar to--

Column 21, Line 19, "nucleic acds to construct" should be changed to --nucleic acids to construct--

Column 22, Line 3, "(T-FAM) CA" should be changed to --(T-FAM)-CA--

Column 22, Line 8, "CACAGCACGACTCAGATGG;" should be changed to
--CACAGCACGACTCAGATGG);--

Column 26, Line 39, "human pappiloma virus," should be changed to --human papilloma virus,--

Column 26, Line 47, "src, one, as" should be changed to --src, onc, as--

Column 26, Line 56, "*Clostridium perfringins*," should be changed to --*Clostridium perfringens*--

Column 27, Line 25, "in FIG. 8 can" should be changed to --in FIG. 13 can--

Column 27, Line 45, "of TC:P is" should be changed to --of T_C:P is--

Column 29, Line 3, "the AG(L/P) contribution," should be changed to --the $\Delta$G(L/P) contribution,--

Column 29, Line 34, "$\lambda i=c/\lambda i$, where" should be changed to --$\lambda i=c/vi$, where--

Column 35, Line 52, "human pappiloma" should be changed to --human papilloma--

Signed and Sealed this
Twelfth Day of June, 2012

David J. Kappos
*Director of the United States Patent and Trademark Office*

CERTIFICATE OF CORRECTION (continued)
U.S. Pat. No. 8,080,379 B2

Column 35, Line 65, "*Clostridium perfringins*," should be changed to --*Clostridium perfringens*,--

Column 37, Line 34, "human pappiloma" should be changed to --human papilloma--

Column 37, Line 47, "*Clostridium perfringins*," should be changed to --*Clostridium perfringens*,--

Column 38, Line 25, "human pappiloma" should be changed to --human papilloma--

Column 38, Line 38, "*Clostridium perfringins*," should be changed to --*Clostridium perfringens*,--

SEQUENCE LISTING

<160> NUMBER OF SEQ ID NOS: 9

<210> SEQ ID NO 1
<211> LENGTH: 36
<212> TYPE: DNA
<213> ORGANISM: Artificial Sequence
<220> FEATURE:

```
<223> OTHER INFORMATION: Chemically synthesized mixed DNA/RNA sequence
<220> FEATURE:
<221> NAME/KEY: misc_feature
<222> LOCATION: (1)...(1)
<223> OTHER INFORMATION: dabsyl attached at 5'-phosphate
<220> FEATURE:
<221> NAME/KEY: misc_feature
<222> LOCATION: (17)...(17)
<223> OTHER INFORMATION: modified with 6-hydroxy fluorescein

<400> SEQUENCE: 1
gctagccacc gctagctcac agcacgactc agatgg                                36

<210> SEQ ID NO 2
<211> LENGTH: 36
<212> TYPE: DNA
<213> ORGANISM: Artificial Sequence
<220> FEATURE:
<223> OTHER INFORMATION: Chemically synthesized mixed DNA/RNA sequence
<220> FEATURE:
<221> NAME/KEY: misc_feature
<222> LOCATION: (1)...(1)
<223> OTHER INFORMATION: dabsyl attached at 5'-phosphate
<220> FEATURE:
<221> NAME/KEY: misc_feature
<222> LOCATION: (17)...(17)
<223> OTHER INFORMATION: modified with 6-hydroxy fluorescein

<400> SEQUENCE: 2
gcatgcctcc gcatgctcac agcacgactc agatgg                                36

<210> SEQ ID NO 3
<211> LENGTH: 36
<212> TYPE: DNA
<213> ORGANISM: Artificial Sequence
<220> FEATURE:
<223> OTHER INFORMATION: Chemically synthesized mixed DNA/RNA sequence
<220> FEATURE:
<221> NAME/KEY: misc_feature
<222> LOCATION: (1)...(1)
<223> OTHER INFORMATION: dabsyl attached at 5'-phosphate
<220> FEATURE:
<221> NAME/KEY: misc_feature
<222> LOCATION: (17)...(17)
<223> OTHER INFORMATION: modified with 6-hydroxy fluorescein

<400> SEQUENCE: 3
gctatccacc gatagctcac agcacgactc agatgg                                36

<210> SEQ ID NO 4
<211> LENGTH: 36
<212> TYPE: DNA
<213> ORGANISM: Artificial Sequence
<220> FEATURE:
<223> OTHER INFORMATION: Chemically synthesized mixed DNA/RNA sequence
<220> FEATURE:
<221> NAME/KEY: misc_feature
<222> LOCATION: (1)...(1)
<223> OTHER INFORMATION: dabsyl attached at 5'-phosphate
<220> FEATURE:
<221> NAME/KEY: misc_feature
<222> LOCATION: (17)...(17)
<223> OTHER INFORMATION: modified with 6-hydroxy fluorescein

<400> SEQUENCE: 4
gcttgccacc gcaagctcac agcacgactc agatgg                                36

<210> SEQ ID NO 5
<211> LENGTH: 38
<212> TYPE: DNA
<213> ORGANISM: Artificial Sequence
<220> FEATURE:
```

```
<223> OTHER INFORMATION: Chemically synthesized mixed DNA/RNA sequence
<220> FEATURE:
<221> NAME/KEY: misc_feature
<222> LOCATION: (1)...(1)
<223> OTHER INFORMATION: dabsyl attached at 5'-phosphate
<220> FEATURE:
<221> NAME/KEY: misc_feature
<222> LOCATION: (19)...(19)
<223> OTHER INFORMATION: modified with 6-hydroxy fluorescein

<400> SEQUENCE: 5
gctagccaaa acgctagctc acagcacgac tcagatgg                              38

<210> SEQ ID NO 6
<211> LENGTH: 33
<212> TYPE: DNA
<213> ORGANISM: Artificial Sequence
<220> FEATURE:
<223> OTHER INFORMATION: Chemically synthesized

<400> SEQUENCE: 6
ccatctgagt cgtgcacgcu agcgguggcu agc                                   33

<210> SEQ ID NO 7
<211> LENGTH: 40
<212> TYPE: DNA
<213> ORGANISM: Artificial Sequence
<220> FEATURE:
<223> OTHER INFORMATION: Chemically synthesized DNA/RNA hybrid
<220> FEATURE:
<221> NAME/KEY: misc_feature
<222> LOCATION: (1)...(1)
<223> OTHER INFORMATION: labelled with 6-hydroxy fluorescein
<220> FEATURE:
<221> NAME/KEY: misc_feature
<222> LOCATION: (17)...(17)
<223> OTHER INFORMATION: dabsyl replaced 5-methyl of T

<400> SEQUENCE: 7
gctatccacc gatagctcca acacgcuagc gguggcuagc                            40

<210> SEQ ID NO 8
<211> LENGTH: 55
<212> TYPE: PRT
<213> ORGANISM: HIV-1

<400> SEQUENCE: 8

Met Gln Lys Gly Asn Phe Arg Asn Gln Arg Lys Thr Val Lys Cys Phe
 1               5                  10                  15

Asn Cys Gly Lys Glu Gly His Ile Ala Lys Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn
    50                  55

<210> SEQ ID NO 9
<211> LENGTH: 154
<212> TYPE: RNA
<213> ORGANISM: HIV-1

<400> SEQUENCE: 9
ggagcucucu cgacgcagga cucggcuugc ugaagcgcgc acggcaagag gcgaggggcg      60
gcgacuggug aguacgccaa aaauuuugac uagcggaggc uagaaggaga gagaugggug     120
cgagagcguc aguauuaagc gggggagaau uaga                                 154
```